United States Patent
Manning et al.

(10) Patent No.: US 10,294,271 B1
(45) Date of Patent: May 21, 2019

(54) COMPOUND, COMPOSITION, AND METHOD FOR DETECTING CASPASE ACTIVITY AND/OR APOPTOSIS

(71) Applicant: Vanderbilt University, Nashville, TN (US)

(72) Inventors: H. Charles Manning, Nashville, TN (US); Matthew R. Hight, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 42 days.

(21) Appl. No.: 14/183,480

(22) Filed: Feb. 18, 2014

Related U.S. Application Data

(60) Provisional application No. 61/765,608, filed on Feb. 15, 2013.

(51) Int. Cl.
| | | |
|---|---|---|
| *A61K 38/06* | (2006.01) | |
| *A61K 38/07* | (2006.01) | |
| *A61K 38/00* | (2006.01) | |
| *A61P 43/00* | (2006.01) | |
| *G01N 33/573* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 5/10* | (2006.01) | |
| *C07K 5/08* | (2006.01) | |

(52) U.S. Cl.
CPC ............... *C07K 5/10* (2013.01); *C07K 5/08* (2013.01); *G01N 33/573* (2013.01)

(58) Field of Classification Search
None
See application file for complete search history.

(56) References Cited

FOREIGN PATENT DOCUMENTS

CN          102626522 A   *   8/2012

OTHER PUBLICATIONS

Translation of portion of CN102626522A.*
Amstad et al. "Detection of Caspase-Activation in Situ by Fluorochrome-Labeled Caspase Inhibitors" BioTechniques 31:608-616. Published Sep. 2001.*
Shekhawat et al. "A Comprehensive Panel of Turn-On Caspase Biosensors for Investigating Caspase Sensitivity and Caspase Activation Pathways" ChemBioChem 12:2353-2364. Published 2011.*
Hight et al. "A peptide-based positron emission tomography (PET) probe for caspase activity detection" Presentation No. SS 65, Scientific Session 11: Chemistry & Imaging Probes—Nuclear Imaging, presented Sep. 20, 2013.*
Wells et al. "Evaluation of caspase inhibitor [18F]FET-VAD-FMK as an imaging agent for apoptosis" J. Nucl. Med. 54:1348. Published May 2013.*
Witte et al. "Bodipy-VAD-Fmk, a useful tool to study yeast peptide N-glycanase activity" Org. Biomol. Chem. 5:3690-3697. Published 2007.*
Serim et al. "Activity-Based Probes for the Study of Proteases: Recent Advances and Developments" ChemMedChem 7:1146-1159. Published 2012.*
Serim et al. "Activity-Based Probes for the Study of Proteases: Recent Advances and Developments" ChemMedChem 7:1146-1159. Published Mar. 19, 2012.*
Araujo et al. "Optimization of a convenient route to produce N-succinimidyl 4-radiodobenzoate for radioiodination of proteins" Applied Radiation and Isotopes 58:667-673. (Year: 2003).*
Baldwin et al. "PET and SPECT Ligands for Imaging Apoptosis" Dept. of Health and Human Services. Contract 1R41MH085768-01. (Year: 2010).*
Allen AM, Ben-Ami M, Reshef A, Steinmetz A, Kundel Y, Inbar E, et al. Assessment of response of brain metastases to radiotherapy by PET imaging of apoptosis with (1)(8)F-ML-10. Eur J Nucl Med Mol Imaging. 2012;39:1400-8.
Amstad PA, Yu G, Johnson GL, Lee BW, Dhawan S, Phelps DJ. Detection of caspase activation in situ by fluorochrome-labeled caspase inhibitors. Biotechniques. 2001;31:608-10, 12, 14, passim.
Ayers GD, McKinley ET, Zhao P, Fritz JM, Metry RE, Deal BC, et al. Volume of preclinical xenograft tumors is more accurately assessed by ultrasound imaging than manual caliper measurements. J Ultrasound Med. 2010;29:891-901.
Balasubramanian K, Mirnikjoo B, Schroit AJ. Regulated externalization of phosphatidylserine at the cell surface: implications for apoptosis. J Biol Chem. 2007;282:18357-64.
Balasubramanian K, Schroit AJ. Aminophospholipid asymmetry: A matter of life and death. Annu Rev Physiol. 2003;65:701-34.
Bauwens M, De Saint-Hubert M, Devos E, Deckers N, Reutelingsperger C, Mortelmans L, et al. Site-specific 68Ga-labeled Annexin A5 as a PET imaging agent for apoptosis. Nucl Med Biol. 2011;38:381-92.
Bedner E, Smolewski P, Amstad P, Darzynkiewicz Z. Activation of caspases measured in situ by binding of fluorochrome-labeled inhibitors of caspases (FLICA): correlation with DNA fragmentation. Exp Cell Res. 2000;259:308-13.
Blankenberg FG, Vanderheyden JL, Strauss HW, Tait JF. Radiolabeling of HYNIC-annexin V with technetium-99m for in vivo imaging of apoptosis. Nat Protoc. 2006;1:108-10.
Blankenberg FG. In vivo detection of apoptosis. J Nucl Med. 2008;49 Suppl 2:81S-95S.
Boersma HH, Kietselaer BL, Stolk LM, Bennaghmouch A, Hofstra L, Narula J, et al. Past, present, and future of annexin A5: from protein discovery to clinical applications. J Nucl Med. 2005;46:2035-50.
Bollag G, Hirth P, Tsai J, Zhang J, Ibrahim PN, Cho H, et al. Clinical efficacy of a RAF inhibitor needs broad target blockade in BRAF-mutant melanoma. Nature. 2010;467:596-9.

(Continued)

*Primary Examiner* — Zachary J Miknis
(74) *Attorney, Agent, or Firm* — Stites & Harbison PLLC; Richard S. Myers, Jr.

(57) ABSTRACT

Molecular probe suitable for quantification of caspase activity in vivo using positron emission tomography (PET). Embodiments of the present invention can detect apoptosis in tumors and as a novel, potentially translatable biomarker for predicting response to personalized medicine.

14 Claims, 11 Drawing Sheets

(56) References Cited

OTHER PUBLICATIONS

Bosman FT, Visser BC, van Oeveren J. Apoptosis: pathophysiology of programmed cell death. Pathol Res Pract. 1996;192:676-83.
Buck JR, Saleh S, Uddin MI, Manning HC. Rapid, Microwave-Assisted Organic Synthesis of Selective (V600E)BRAF Inhibitors for Preclinical Cancer Research. Tetrahedron Lett. 2012;53:4161-5.
Chang J, Ormerod M, Powles TJ, Allred DC, Ashley SE, Dowsett M. Apoptosis and proliferation as predictors of chemotherapy response in patients with breast carcinoma. Cancer. 2000;89:2145-52.
Chen DL, Zhou D, Chu W, Herrbrich P, Engle JT, Griffin E, et al. Radiolabeled isatin binding to caspase-3 activation induced by anti-Fas antibody. Nucl Med Biol. 2012;39:137-44.
Chen DL, Zhou D, Chu W, Herrbrich PE, Jones LA, Rothfuss JM, et al. Comparison of radiolabeled isatin analogs for imaging apoptosis with positron emission tomography. Nucl Med Biol. 2009;36:651-8.
Cotter TG. Apoptosis and cancer: the genesis of a research field. Nat Rev Cancer. 2009;9:501-7.
Dillon SR, Constantinescu A, Schlissel MS. Annexin V binds to positively selected B cells. J Immunol. 2001;166:58-71.
Duprez L, Wirawan E, Vanden Berghe T, Vandenabeele P. Major cell death pathways at a glance. Microbes Infect. 2009;11:1050-62.
Eckelman WC, Reba RC, Kelloff GJ. Targeted imaging: an important biomarker for understanding disease progression in the era of personalized medicine. Drug Discov Today. 2008;13:748-59.
Ekert PG, Silke J, Vaux DL. Caspase inhibitors. Cell Death Differ. 1999;6:1081-6.
Elliott JI, Surprenant A, Marelli-Berg FM, Cooper JC, Cassady-Cain RL, Wooding C, et al. Membrane phosphatidylserine distribution as a non-apoptotic signalling mechanism in lymphocytes. Nat Cell Biol. 2005;7:808-16.
Ganesan R, Jelakovic S, Campbell AJ, Li ZZ, Asgian JL, Powers JC, et al. Exploring the S4 and S1 prime subsite specificities in caspase-3 with aza-peptide epoxide inhibitors. Biochemistry. 2006;45:9059-67.
Garcia-Calvo M, Peterson EP, Leiting B, Ruel R, Nicholson DW, Thornberry NA. Inhibition of human caspases by peptide-based and macromolecular inhibitors. J Biol Chem. 1998;273:32608-13.
Haberkorn U, Kinscherf R, Krammer PH, Mier W, Eisenhut M. Investigation of a potential scintigraphic marker of apoptosis: radioiodinated Z-Val-Ala-DL-Asp(O-methyl)-fluoromethyl ketone. Nucl Med Biol. 2001;28:793-8.
Hanahan D, Weinberg RA. Hallmarks of cancer: the next generation. Cell. 2011;144:646-74.
Hoglund J, Shirvan A, Antoni G, Gustaysson SA, Langstrom B, Ringheim A, et al. 18F-ML-10, a PET tracer for apoptosis: first human study. J Nucl Med. 2011;52:720-5.
Ke S, Wen X, Wu QP, Wallace S, Charnsangavej C, Stachowiak AM, et al. Imaging taxane-induced tumor apoptosis using PEGylated, 111In-labeled annexin V. J Nucl Med. 2004;45:108-15.
Lawson VA, Haigh CL, Roberts B, Kenche VB, Klemm HM, Masters CL, et al. Near-infrared fluorescence imaging of apoptotic neuronal cell death in a live animal model of prion disease. ACS Chem Neurosci. 2010;1:720-7.
Manning HC, Merchant NB, Foutch AC, Virostko JM, Wyatt SK, Shah C, et al. Molecular imaging of therapeutic response to epidermal growth factor receptor blockade in colorectal cancer. Clin Cancer Res. 2008;14:7413-22.
McKinley ET, Smith RA, Zhao P, Fu A, Saleh SA, Uddin MI, et al. 3'-Deoxy-3'-18F-fluorothymidine PET predicts response to (V600E)BRAF-targeted therapy in preclinical models of colorectal cancer. J Nucl Med. 2013;54:424-30.
Mortlock AA, Foote KM, Heron NM, Jung FH, Pasquet G, Lohmann JJ, et al. Discovery, synthesis, and in vivo activity of a new class of pyrazoloquinazolines as selective inhibitors of aurora B kinase. J Med Chem. 2007;50:2213-24.
Nguyen QD, Challapalli A, Smith G, Fortt R, Aboagye EO. Imaging apoptosis with positron emission tomography: 'bench to bedside' development of the caspase-3/7 specific radiotracer [(18)F]ICMT-11. Eur J Cancer. 2012;48:432-40.
Nguyen QD, Smith G, Glaser M, Perumal M, Arstad E, Aboagye EO. Positron emission tomography imaging of drug-induced tumor apoptosis with a caspase-3/7 specific [18F]-labeled isatin sulfonamide. Proc Natl Acad Sci U S A. 2009;106:16375-80.
Pereira NA, Song Z. Some commonly used caspase substrates and inhibitors lack the specificity required to monitor individual caspase activity. Biochem Biophys Res Commun. 2008;377:873-7.
Peterson TE, Manning HC. Molecular imaging: 18F-FDG PET and a whole lot more. J Nucl Med Technol. 2009;37:151-61.
Rauber P, Angliker H, Walker B, Shaw E. The synthesis of peptidylfluoromethanes and their properties as inhibitors of serine proteinases and cysteine proteinases. Biochem J. 1986;239:633-40.
Ren YG, Wagner KW, Knee DA, Aza-Blanc P, Nasoff M, Deveraux QL. Differential regulation of the TRAIL death receptors DR4 and DR5 by the signal recognition particle. Mol Biol Cell. 2004;15:5064-74.
Reshef A, Shirvan A, Akselrod-Ballin A, Wall A, Ziv I. Small-molecule biomarkers for clinical PET imaging of apoptosis. J Nucl Med. 2010;51:837-40.
Schutters K, Reutelingsperger C. Phosphatidylserine targeting for diagnosis and treatment of human diseases. Apoptosis. 2010;15:1072-82.
Shah C, Miller TW, Wyatt SK, McKinley ET, Olivares MG, Sanchez V, et al. Imaging biomarkers predict response to anti-HER2 (ErbB2) therapy in preclinical models of breast cancer. Clin Cancer Res. 2009;15:4712-21.
Smolewski P, Bedner E, Du L, Hsieh TC, Wu JM, Phelps DJ, et al. Detection of caspases activation by fluorochrome-labeled inhibitors: Multiparameter analysis by laser scanning cytometry. Cytometry. 2001;44:73-82.
Su H, Chen G, Gangadharmath U, Gomez LF, Liang Q, Mu F, et al. Evaluation of [(18)F]-CP18 as a PET imaging tracer for apoptosis. Mol Imaging Biol. 2013;15:739-47.
Tsai J, Lee JT, Wang W, Zhang J, Cho H, Mamo S, et al. Discovery of a selective inhibitor of oncogenic B-Raf kinase with potent antimelanoma activity. Proc Natl Acad Sci U S A 2008;105:3041-6.
Wang Z, Watt W, Brooks NA, Harris MS, Urban J, Boatman D, et al. Kinetic and structural characterization of caspase-3 and caspase-8 inhibition by a novel class of irreversible inhibitors. Biochim Biophys Acta. 2010;1804:1817-31.
Waterhouse RN, Mardon K, Giles KM, Collier TL, O'Brien JC. Halogenated 4-(phenoxymethyl)piperidines as potential radiolabeled probes for sigma-1 receptors: in vivo evaluation of [1231]-1-(iodopropen-2-yl)-4-[(4-cyanophenoxy)methyl] pip eri dine. J Med Chem. 1997;40:1657-67.
Wilkinson RW, Odedra R, Heaton SP, Wedge SR, Keen NJ, Crafter C, et al. AZD1152, a selective inhibitor of Aurora B kinase, inhibits human tumor xenograft growth by inducing apoptosis. Clin Cancer Res. 2007;13:3682-8.
Xia CF, Chen G, Gangadharmath U, Gomez LF, Liang Q, Mu F, et al. In vitro and in vivo evaluation of the caspase-3 substrate-based radiotracer [(18)F]-CP18 for PET imaging of apoptosis in tumors. Mol Imaging Biol. 2013;15:748-57.
Xu J, Li K, Smith RA, Waterton JC, Zhao P, Chen H, et al. Characterizing tumor response to chemotherapy at various length scales using temporal diffusion spectroscopy. PLoS One. 2012;7:e41714.
Yagle KJ, Eary JF, Tait JF, Grierson JR, Link JM, Lewellen B, et al. Evaluation of 18F-annexin V as a PET imaging agent in an animal model of apoptosis. J Nucl Med. 2005;46:658-66.
Krieger, et al.; Identification of a cyclic nucleotide- and voltage-activated ion channel from insect antennae; Insect Biochemistry and Molecular Biology; 29; 1999; pp. 255-267.

* cited by examiner

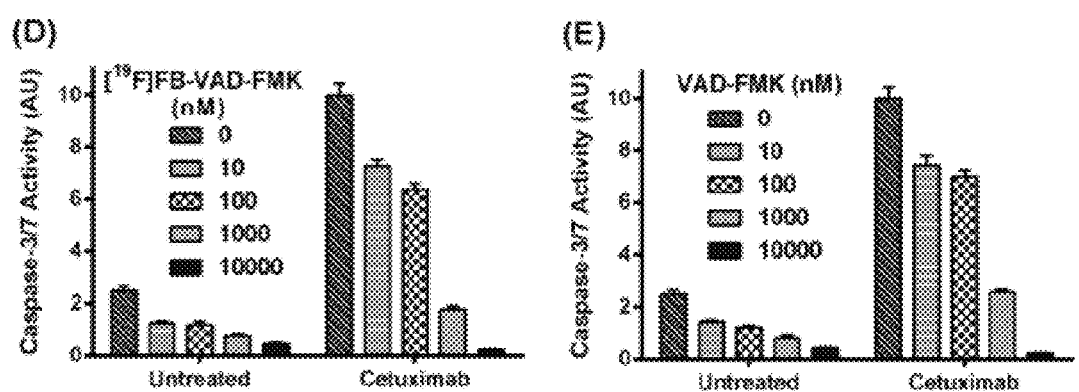
Figure 1 (Con't)

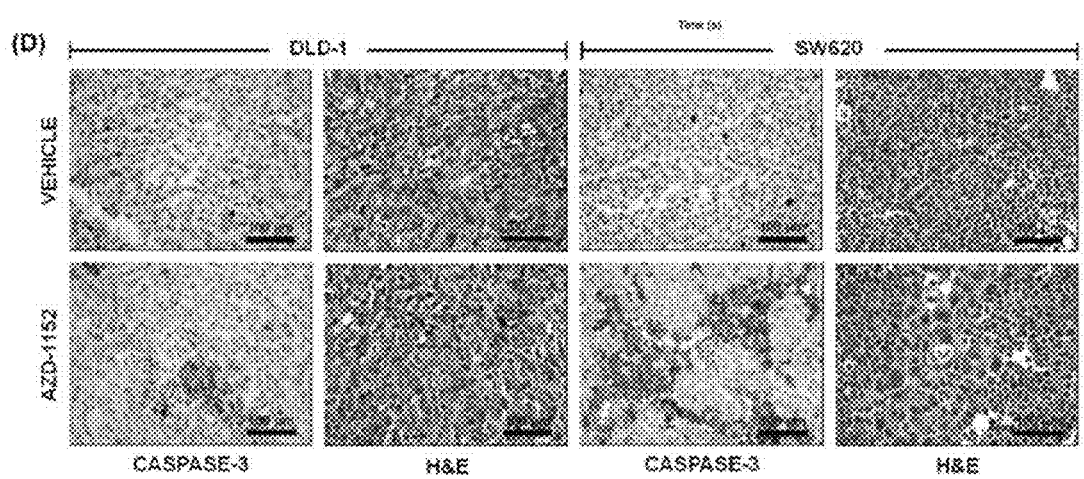
Figure 4 (Con't)

COMPOUND, COMPOSITION, AND METHOD FOR DETECTING CASPASE ACTIVITY AND/OR APOPTOSIS

PRIOR APPLICATIONS

This application claims benefit to U.S. Patent Application Number 61/765,608, filed Feb. 15, 2013, the contents of which are incorporated herein by reference.

GOVERNMENT INTEREST

This invention was made with government support under R01-CA140628, RC1-CA145138, K25-CA127349, P50-CA128323, P50-CA95103, U24-CA126588, S10-RR17858, R41-MH85768, 5P30 DK058404, and R25-CA136440 awarded by the National Institutes of Health. The government has certain rights in the invention.

INTRODUCTION

Cell death proceeds through multiple, mechanistically distinct processes that include necrosis, autophagy, mitotic catastrophe, and apoptosis. Apoptosis, or programmed cell death, is an orchestrated process that facilitates elimination of unnecessary, damaged, or compromised cells to confer an overall advantage to the host organism. As such, apoptosis is an essential component of embryonic development, tissue homeostasis, and immunological competence. Deviations from normal apoptotic programs are frequently associated with human diseases such as cancer. Since many anti-cancer therapies aim to selectively induce apoptosis in tumor cells, there is a long felt need for quantitative, non-invasive imaging biomarkers that reflect apoptosis. Embodiments of the present invention meet that need by improving drug discovery and predict early responses in patients.

Because of the aforementioned need, clinically robust molecular imaging biomarkers of apoptosis have been sought after for many years, but none have yet proven optimal. Classically, molecular imaging measures of apoptosis have relied upon labeled forms of the 36 kDa protein Annexin V, which binds to externalized phosphatidylserine on the plasma membrane of cells undergoing apoptosis. Though functionalization of Annexin V for optical, single-photon emission computed tomography (SPECT), and positron emission tomography (PET) imaging have been reported, imaging probes based on Annexin V generally suffer from limitations that include suboptimal biodistribution and pharmacokinetics, calcium ion-dependency, and a lack of specificity. Another promising approach that capitalizes upon cell membrane alterations associated with apoptosis utilizes a small molecule known as $^{18}$F-ML-10, which has been evaluated in a limited number of patients. The strengths and weaknesses of this approach are under investigation at a number of institutions.

Other intracellular molecular targets within the apoptosis signaling cascade represent opportunities for molecular probe development. For example, as regulators of extrinsic and intrinsic apoptosis, caspases have been suggested as promising targets for molecular imaging and for drug development. Embodiments of the present invention demonstrate the utility of a peptide-based pan-caspase inhibitor, the modified tripeptide sequence Val-Ala-Asp(OMe)-fluoromethylketone (VAD-FMK), as the basis for developing a PET imaging probe for detecting apoptosis. For example, one embodiment of the invention is [$^{18}$F]4-fluorobenzylcarbonyl-Val-Ala-Asp(OMe)-fluoromethylketone ([$^{18}$F]FB-VAD-FMK), a novel and translatable molecular probe that enables quantification of caspase activity in vivo using, for example, PET imaging. Utilizing small animal microPET imaging of multiple models of human colorectal cancer (CRC), the inventors show that in vivo tumor accumulation of [$^{18}$F]FB-VAD-FMK accurately reflects elevated caspase-3 activity in response to Aurora B kinase inhibition as well as a multi-drug regimen that combined an inhibitor of mutant BRAF and a dual PI3K/mTOR inhibitor.

SUMMARY OF THE INVENTION

Deviations from normal cell death programs tend to promote cell survival and are frequently associated with cancer. Many anti-cancer medicines aim to selectively induce cell death in tumor cells, but highly validated non-invasive biomarkers to assess such molecular events are lacking. Embodiments of the present invention include novel positron emission tomography (PET) molecular imaging agents that allow non-invasive, targeted detection of caspase activation and tumor cell death following effective drug treatment. Embodiments of the present invention can be used within the context of molecularly targeted therapy as well as conventional therapeutics and thus used to predict individualized responses in patients and accelerate the development of improved cancer therapies.

Thus one aspect of the present invention is a method for imaging a molecular event in a sample, comprising administering to said sample a probe having an affinity for a target, the probe comprising a compound of the preset invention, and then detecting a signal from said probe. In certain embodiments of the invention, the compound is a substituted Val-Ala-Asp(OMe)-fluoromethylketone core. In certain embodiments of the invention, the molecular event is caspase activity.

Another aspect of the invention is a method of imaging a molecular event in a sample, comprising administering to said sample a probe having an affinity for a target, the probe being selected from substituted Val-Ala-Asp(OMe)-fluoromethylketone and pharmaceutically acceptable salts thereof; and detecting a signal from said probe.

Another aspect of the invention are compounds, including those of the following formula:

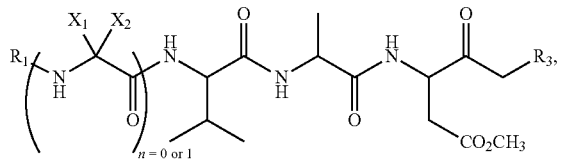

wherein the variables are defined herein.

Another aspect of the invention are pharmaceutical compositions, which include the compounds of the present invention, or pharmaceutically acceptable salts therof, combined with a pharmaceutically acceptable carrier.

Another aspect of the present invention is a method quantifying the progression of a disease state in a subject, comprising administering to a first sample of the subject a probe having an affinity for a target, the probe comprising a compound of the present invention, detecting a signal from said probe; after a period of time administering to a second sample of the subject a probe having an affinity for a target, detecting a second signal, and then comparing the first signal with the second signal to determine the progress of a disease state. In certain embodiments, the compound of the present invention is a compound is a substituted Val-Ala-Asp (OMe)-fluoromethylketone core.

Another aspect of the present invention is a method for determining the presence of a disease state, comprising administering to a first sample of the subject a probe having an affinity for a target, and detecting a signal from said probe.

In embodiments of the invention, the disease state is cancer, including breast, brain and colorectal cancer.

DESCRIPTION OF THE INVENTION

Figure 1:
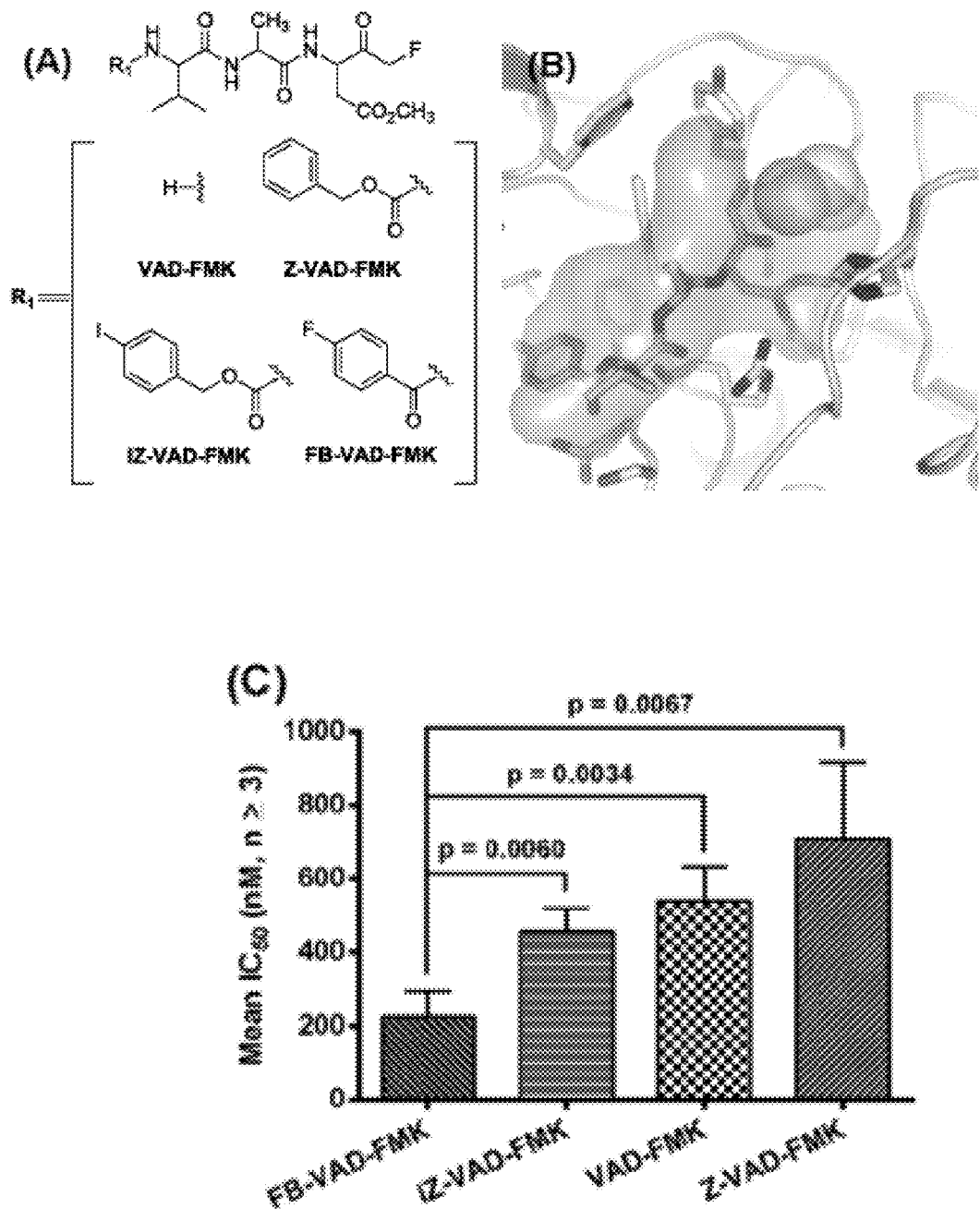
FIG. 1. Prioritization of FB-modified VAD-FMK peptide caspase inhibitor. Chemical structures for R1 substitution of examples of VAD-FMK peptide inhibitor scaffolds of the present invention (A). FB-VAD-FMK (green capped sticks) shown docked into the caspase-3 protein structure with covalent inhibitor removed (PDB ID 3KJF); covalent inhibitor protein attachment at Cys163 is shown in yellow and white VDW spheres. Atom colors: oxygen=red; nitrogen=blue; carbon=grey. Grey VDW surfaces indicate the space-filling shape of the covalent bound inhibitor in PDB ID 3KJF (B). Mean $IC_{50}$ values (n≥3) of inhibition of human recombinant caspase-3 by VAD-FMK and analogues as assessed using a luminescence biochemistry assay-based method (Conc=concentration) (C). Caspase-3/7 inhibition with [$^{19}$F]FB-VAD-FMK (D) or VAD-FMK (E) in untreated or cetuximab-treated DiFi cells (n=4).

The presently-disclosed subject matter further includes a method of imaging a molecular event, which involves administering a probe with an affinity for a target, the probe being selected from a compound and/or the a pharmaceutical composition as described herein, or a pharmaceutically acceptable salt thereof, or a pharmaceutically acceptable derivative thereof; and detecting a signal from the probe.

In some embodiments of the method, the sample is at least one of a cell or a tissue. In some embodiments of the method, the administration method is in vivo or in vitro. In some embodiments of the method, the detecting step is with PET imaging.

In some embodiments of the method, the molecular event is selected from caspase activity and apoptosis. In some embodiments of the method, the method further involves quantifying caspase activity and/or apoptosis. In some embodiments of the method, the caspase activity and/or apoptosis is caspase activity in a tumor and/or apoptosis in a tumor. In some embodiments of the method, the method further involves analyzing the signal to determine therapeutic efficacy.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" included a plurality of such cells, and so forth.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In one aspect, the invention relates to compounds, or pharmaceutically acceptable derivatives thereof, useful as in methods for detecting caspase activity and/or apoptosis, including quantifying and/or imaging caspase activity and/or apoptosis in a tumor in vivo. In general, it is contemplated that each disclosed derivative and variable (R groups, for example) is independent and can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect of the present invention, the invention relates to compounds having a structure represented by formula (II):

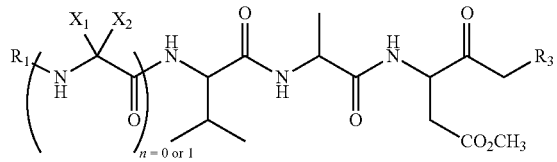

including wherein $R_1$ is selected from C—$R_5$-halogen, CO—$R_5$-halogen, CO—$R_5$—$R_6$-halogen, CO—$R_6$, O—$R_6$, O—$R_6R_6$, $SO_2$—$R_6R_6$, O—CO—$R_6$, O—$R_6$—O—CO—$R_6$;

$R_3$ is selected from halogen, $R_5$-halogen;

$R_5$ is selected from hydrogen, alkyl, alkoxy, aryl, cycloalkyl, or a $C_{3-8}$ membered ring containing C, O, S and/or N, optionally substituted with one or more R7, CO—$R_6$, O—$R_6$, O—$R_6R_6$, $SO_2$—$R_6R_6$, O—CO—$R_6$, O—$R_6$—O—CO—$R_6$;

$R_6$ is selected from alkyl, aryl, alkoxy, cycloalkyl, or a $C_{3-8}$ membered ring containing C, O, S and/or N, optionally substituted with one or more $R_7$;

$R_7$ is selected from hydrogen, $C_{1-6}$ alkyl, $C_{3-10}$ cycloalkyl, aryl, benzyl, heteroaryl, halogen, CN, $CF_3$, $CONR_5R_5$, $S(O)_{0-2}NR_5R_5$, $CSNH_2$;

$X_2$ is selected from alkyl, alkoxy, $R_5$—$C_{3-8}$ membered ring containing C, O, S and/or N, optionally substituted with one or more $R_7$; and $X_3$ is selected from alkyl, alkoxy, $R_5$—$C_{3-8}$ membered ring containing C, O, S and/or N, optionally substituted with one or more $R_7$;

and pharmaceutically acceptable salts thereof.

In an embodiment of the invention, $R_1$ is selected from

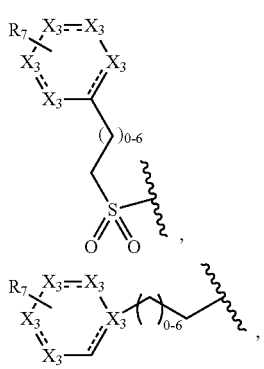

alkyl, CO-alkyl, CO-phenyl, CO-alkyl-phenyl, wherein $X_3$ is C, $CR_7$, N, $NR_7$.

In another embodiment, said $C_{3-8}$ membered ring containing C, O, S and/or N, optionally substituted with one or more $R_7$ is independently heteroaryl, aryl, cycloalkyl, heterocycloalkyl.

In another embodiment, the $C_{3-8}$ membered ring containing C, O, S and/or N is optionally substituted phenyl, pyridinyl, and piperazinyl.

In another embodiment, the compound has a structure represented by formula (I):

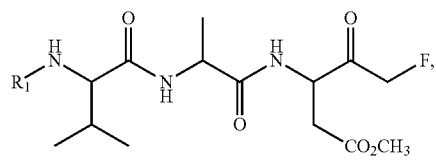

including wherein $R_1$ is selected from the following:

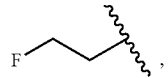

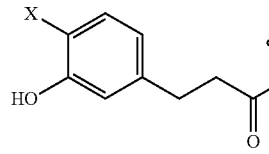

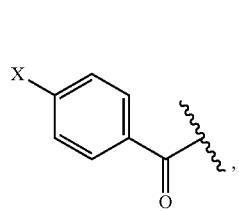

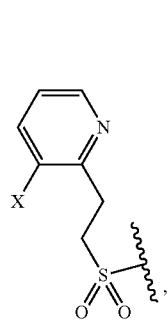

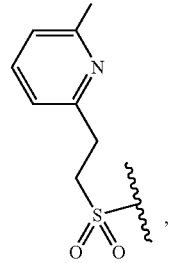

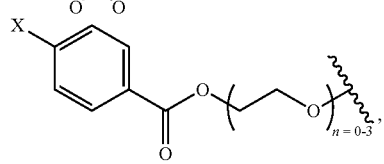

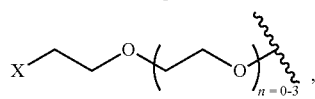

-continued
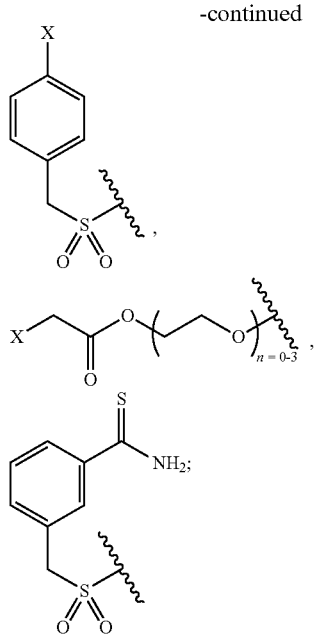
X is iodine or fluorine; and pharmaceutically acceptable salts thereof.
In another embodiment, $R_1$ is selected from the following:
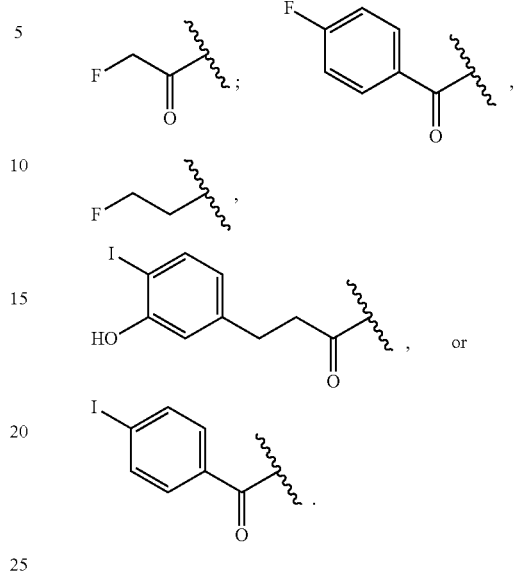
In another embodiment, the compound is at least one of the following:
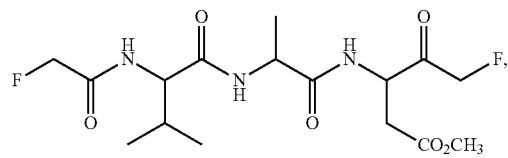
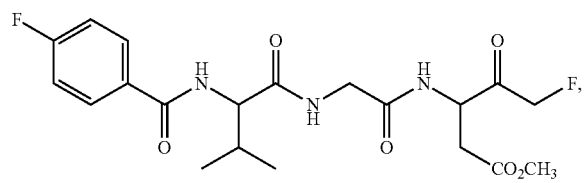
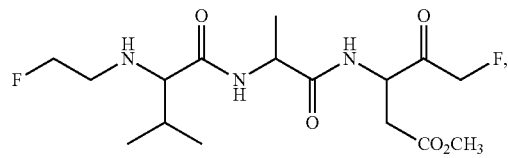
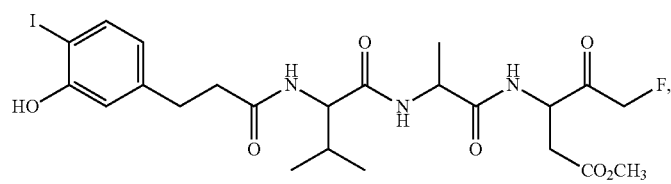
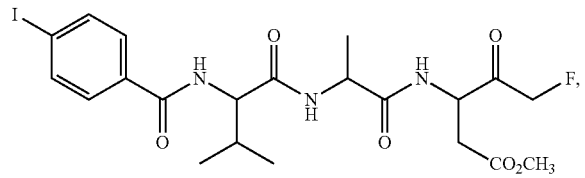

-continued
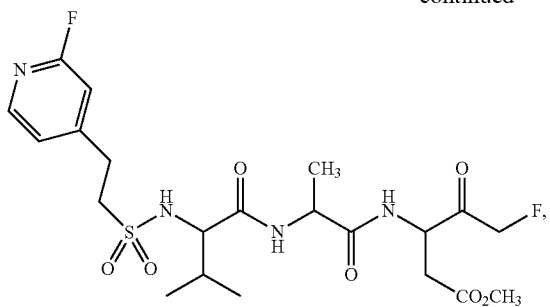
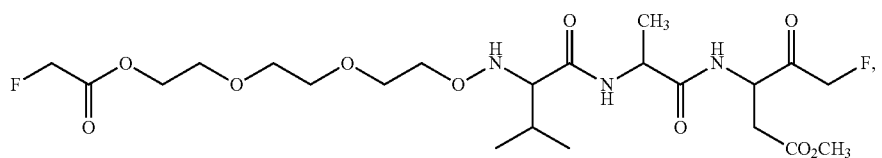
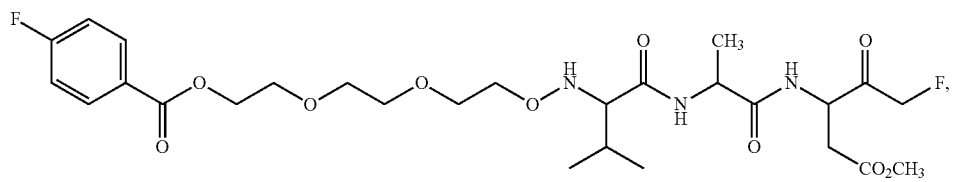
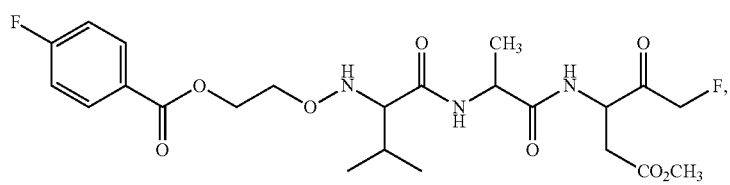
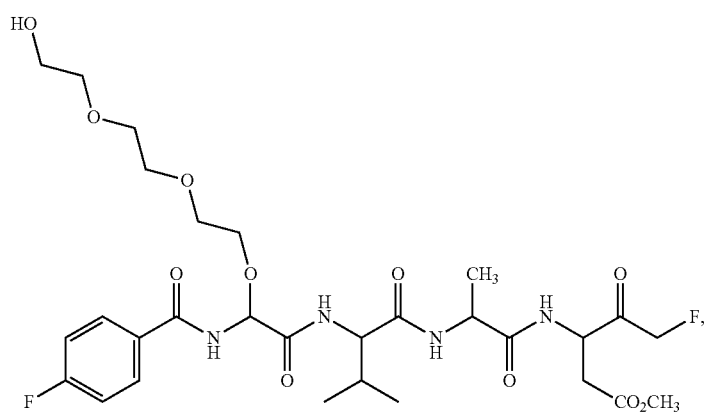
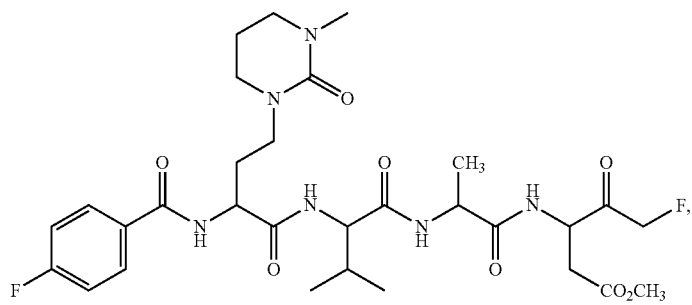

-continued

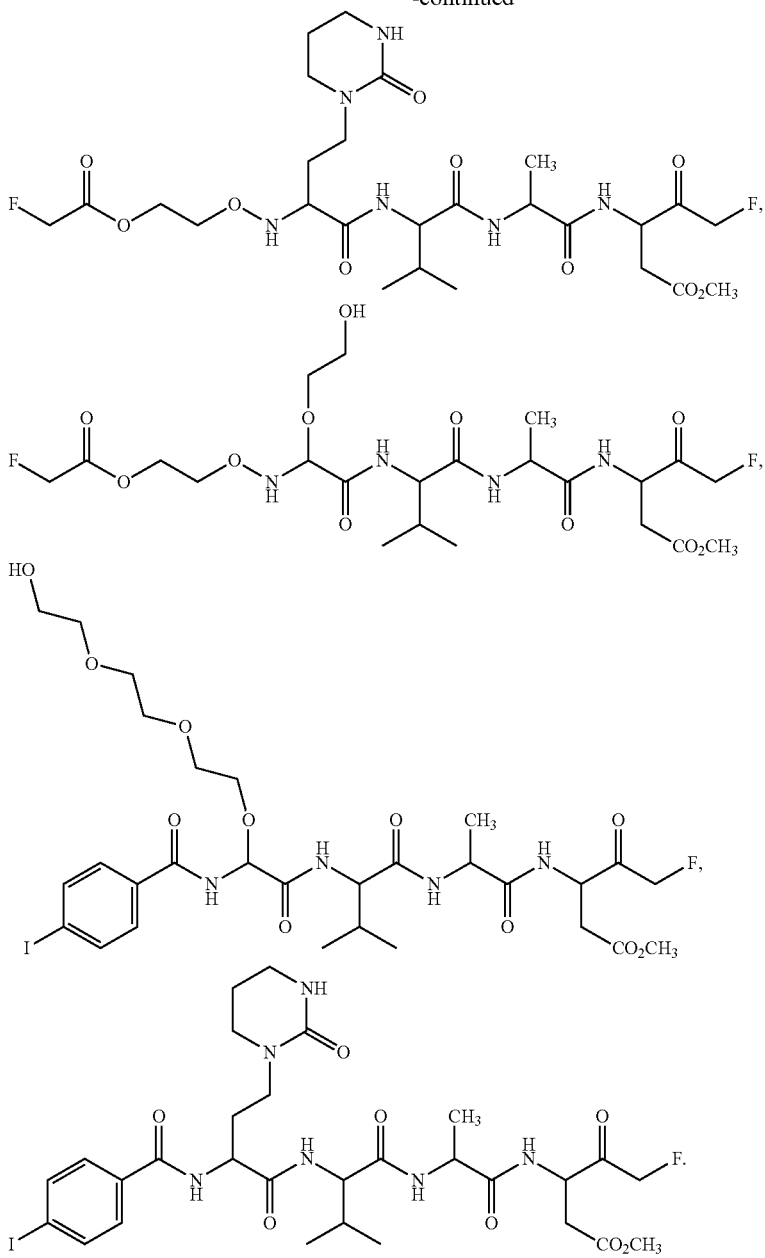

The compounds disclosed herein can include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques By way of example, a tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be coadministered, either in concomitant therapy or in a fixed combination.

Method of Using

As stated above, embodiments of the present invention include methods of using compounds and/or compositions of the present invention.

One aspect of the present invention is a method of imaging a molecular event in a sample, the method steps comprising administering to the sample a probe having an affinity for a target. The probe contacts the target and emits a detectable signal. Thus, after the probe is administered, a signal from the probe may be detected. In embodiments of the present invention, the sample can be at least one of cells, tissue, cellular tissue, serum, cell extract, bodily fluids. The bodily fluids may be, for example, breast milk, sputum, vaginal fluids, urine.

Thus, one aspect of the present invention is a method of imaging a molecular event in a sample, comprising:

(a) administering to said sample a probe having an affinity for a target, the probe being selected from substituted Val-Ala-Asp(OMe)-fluoromethylketone and pharmaceutically acceptable salts thereof; and (b) detecting a signal from said probe.

In embodiments of the invention, the molecular event is caspase activity. Also, in embodiments of the invention, the detecting step is with positron emission tomography (PET).

In other embodiments of the invention, the probe comprises a compound that has a structure represented by formula (II):

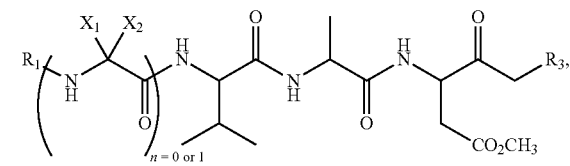

including wherein $R_1$ is selected from C—$R_5$-halogen, CO—$R_5$-halogen, CO—$R_5$—$R_6$-halogen, CO—$R_6$, O—$R_6$, O—$R_6R_6$, $SO_2$—$R_6R_6$, O—CO—$R_6$, O—$R_6$—O—CO—$R_6$;

$R_3$ is selected from halogen, $R_5$-halogen;

$R_5$ is selected from hydrogen, alkyl, alkoxy, aryl, cycloalkyl, or a $C_{3-8}$ membered ring containing C, O, S and/or N, optionally substituted with one or more $R_7$, CO—$R_6$, O—$R_6$, O—$R_6R_6$, $SO_2$—$R_6R_6$, O—CO—$R_6$, O—$R_6$—O—CO—$R_6$;

$R_6$ is selected from alkyl, aryl, alkoxy, cycloalkyl, or a $C_{3-8}$ membered ring containing C, O, S and/or N, optionally substituted with one or more $R_7$;

$R_7$ is selected from hydrogen, $C_{1-6}$ alkyl, $C_{3-10}$ cycloalkyl, aryl, benzyl, heteroaryl, halogen, CN, $CF_3$, $CONR_5R_5$, $S(O)_{0-2}NR_5R_5$, $CSNH_2$;

$X_2$ is selected from alkyl, alkoxy, $R_5$—$C_{3-8}$ membered ring containing C, O, S and/or N, optionally substituted with one or more $R_7$; and $X_3$ is selected from alkyl, alkoxy, $R_5$—$C_{3-8}$ membered ring containing C, O, S and/or N, optionally substituted with one or more $R_7$;

and pharmaceutically acceptable salts thereof.

Another aspect of the present invention is a method of quantifying the progression of a disease state in a subject, comprising:

(a) administering to a first sample of the subject a probe having an affinity for a target, the probe being selected from a substituted Val-Ala-Asp(OMe)-fluoromethylketone;

(b) detecting a signal from said probe;

(c) after a period of time from step (b), administering to a second sample of the subject a probe having an affinity for a target, the probe being selected from a substituted Val-Ala-Asp(OMe)-fluoromethylketone;

(d) detecting a second signal; and (e) comparing the first signal with the second signal to determine the progress of a disease state.

In embodiments of the invention, the sample may be at least one of cells, tissue, cellular tissue, serum, cell extract, bodily fluid.

In other embodiments, the the probe is a compound of the following formula:

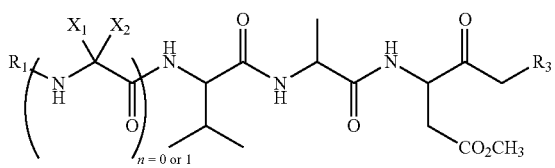

including wherein $R_1$ is selected from C—$R_5$-halogen, CO—$R_5$-halogen, CO—$R_5$—$R_6$-halogen, a $C_{3-8}$ membered ring containing C, O, S and/or N, optionally substituted with one or more $R_7$, CO—$R_6$, O—$R_6$, O—$R_6R_6$, $SO_2$—$R_6R_6$, O—CO—$R_6$, O—$R_6$—O—CO—$R_6$;

$R_3$ is selected from halogen, $R_5$-halogen;

$R_5$ is selected from hydrogen, alkyl, alkoxy, aryl, cycloalkyl, or a $C_{3-8}$ membered ring containing C, O, S and/or N, optionally substituted with one or more $R_7$, CO—$R_6$, O—$R_6$, O—$R_6R_6$, $SO_2$—$R_6R_6$, O—CO—$R_6$, O—$R_6$—O—CO—$R_6$;

$R_6$ is selected from alkyl, aryl, alkoxy, cycloalkyl, or a $C_{3-8}$ membered ring containing C, O, S and/or N, optionally substituted with one or more $R_7$;

$R_7$ is selected from hydrogen, $C_{1-6}$ alkyl, $C_{3-10}$ cycloalkyl, aryl, benzyl, heteroaryl, halogen, CN, $CF_3$, $CONR_5R_5$, $S(O)_{0-2}NR_5R_5$, $CSNH_2$;

$X_2$ is selected from alkyl, alkoxy, $R_5$—$C_{3-8}$ membered ring containing C, O, S and/or N, optionally substituted with one or more $R_7$; and $X_3$ is selected from alkyl, alkoxy, $R_5$—$C_{3-8}$ membered ring containing C, O, S and/or N, optionally substituted with one or more $R_7$;

and pharmaceutically acceptable salts thereof; and a pharmaceutical carrier.

Another aspect of the present invention is a method of determining the presence of a disease state, comprising:

(a) administering to a first sample of the subject a probe having an affinity for a target, the probe being a substituted Val-Ala-Asp(OMe)-fluoromethylketone;

(b) detecting a signal from said probe.

In embodiments of the invention, the method further comprising a disease state treatment step either before step (a), after step (b), or both. Also, in certain embodiments, the disease state is cancer.

In other embodiments, the probe is a compound of the following formula:

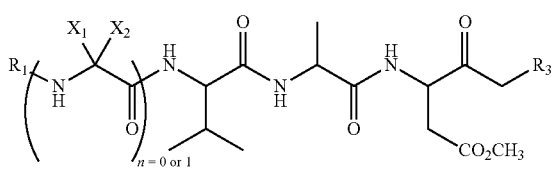

including wherein $R_1$ is selected from C—$R_5$-halogen, CO—$R_5$-halogen, CO—$R_5$—$R_6$-halogen, a $C_{3-8}$ membered ring containing C, O, S and/or N, optionally substituted with one or more $R_7$, CO—$R_6$, O—$R_6$, O—$R_6R_6$, $SO_2$—$R_6R_6$, O—CO—$R_6$, O—$R_6$—O—CO—$R_6$;

$R_3$ is selected from halogen, $R_5$-halogen;

$R_5$ is selected from hydrogen, alkyl, alkoxy, aryl, cycloalkyl, or a $C_{3-8}$ membered ring containing C, O, S and/or N, optionally substituted with one or more $R_7$, CO—$R_6$, O—$R_6$, O—$R_6R_6$, $SO_2$—$R_6R_6$, O—CO—$R_6$, O—$R_6$—O—CO—$R_6$;

$R_6$ is selected from alkyl, aryl, alkoxy, cycloalkyl, or a $C_{3-8}$ membered ring containing C, O, S and/or N, optionally substituted with one or more $R_7$;

$R_7$ is selected from hydrogen, $C_{1-6}$ alkyl, $C_{3-10}$ cycloalkyl, aryl, benzyl, heteroaryl, halogen, CN, $CF_3$, $CONR_5R_5$, $S(O)_{0-2}NR_5R_5$, $CSNH_2$;

$X_2$ is selected from alkyl, alkoxy, $R_5$—$C_{3-8}$ membered ring containing C, O, S and/or N, optionally substituted with one or more $R_7$; and $X_3$ is selected from alkyl, alkoxy, $R_5$—$C_{3-8}$ membered ring containing C, O, S and/or N, optionally substituted with one or more $R_7$;

and pharmaceutically acceptable salts thereof; and a pharmaceutical carrier.

In embodiments of the invention, the disease state can be cancer. In other embodiments of the present invention, the disease state can be brain cancer, breast cancer, colorectal cancer, In the above embodiments and other embodiments of the present invention, the administration step is in vivo or in vitro.

EXPERIMENTAL AND DISCUSSION

The following experimental an discussion section highlights examples of the present invention, demonstrating embodiments of the present invention. The following is intended to be exemplary of the present invention and not intended to be limiting thereof. The following shows that the VAD-FMK peptide is a promising scaffold for molecular imaging of caspase activity and response to molecularly targeted therapy using positron emission tomography. Among these peptides, embodiments of the present invention, including [$^{18}$F]FB-VAD-FMK are effective PET imaging probes for non-invasive quantification of apoptosis in tumors and represent a translatable biomarker of therapeutic efficacy in personalized medicine.

Materials and Methods

Molecular Modeling

Co-crystal structures for the caspase-3 protein with an aza-peptide epoxide inhibitor (PDB ID 2CNN) and a covalently bound β-strand peptidomimetic inhibitor (PDB ID 3KJF) were obtained from the Brookhaven Protein Data Bank and used to evaluate the potential of prosthetically labeled VAD-FMK, and deviations thereof, to be accommodated within the active caspase-3 binding domain. Structural alignment of both caspase-3 inhibitor co-crystal structures was performed using PyMOL (Molecular Graphics System, Version 1.5.0.4, Schrödinger, LLC) to reveal a minor 0.22 angstrom α-carbon protein backbone coordinate root mean squared deviation (RMSD). Both caspase-3 inhibitor-binding sites were treated as energetically equivalent and the smaller β-strand peptidomimetic inhibitor structure (PDB ID 3KJF) was chosen as the starting point for molecular docking calculations. Following removal of the co-crystallized covalent inhibitor ligand, molecular docking was performed using the high resolution, flexible SurflexDock GeomX protocol as implemented in SYBYL-X 2.0 (Tripos International, 1699 South Hanley Rd., St. Louis, Mo., 63144, USA), with a protomol target based on the β-strand peptidomimetic inhibitor structure with the addition of a 2.0 angstrom bloat parameter. Best scoring energy-minimized docked poses were ranked using the Tripos SYBYL SurflexDock flexible protein scoring function, PF-score (Crash parameter) for FB-VAD-FMK, Z-VAD-FMK, IZ-VAD-FMK and VAD-FMK were determined for comparison of physically plausible, low energy minimized conformations in the bound state across the proposed peptide ligand modifications.

Peptide and Derivatives

[$^{19}$F]FB-VAD-FMK and [$^{127}$I]IZ-VAD-FMK were synthesized as described below. VAD-FMK (American Peptide) and Z-VAD-FMK (TOCRIS Bioscience, #2163) were obtained commercially and used without further purification. Relative enzyme selectivity of [$^{19}$F]FB-VAD-FMK compared to parent peptide was evaluated as described below. Lipophilicity measurements (Log $P_{7.5}$) of peptide derivatives were determined analogously to reported methods and described below.

Biochemical Caspase-3 Inhibition Assay

Caspase-Glo 3/7 (Promega) was employed as a readout of inhibition where by a caspase-cleavable protected luciferase substrate is directly sensitive to caspase-3/7 activity and quantifiable by bioluminescence. Caspase inhibitor dissolved in DMSO (0, 0.1, 1, 10, 100, 1000, or 10000 nM) was combined with recombinant human caspase-3 enzyme (C1224-10UG, Sigma) (100 nM) in 1× phosphate buffered saline (PBS) in microcentrifuge tubes, vortexed, and incubated at 37° C. for 30 min. After incubation, Caspase-Glo 3/7 reagent (Promega) was added in accordance with the manufacturer's instructions. Solutions were vortexed, incubated for an additional 30 min, and dispensed into opaque wall/bottom 384-well plates (BD Biosciences) for measurement of caspase activity. Sample luminescence was measured using a Synergy 4 plate reader (BioTek).

Cellular Caspase Inhibition Assay

DiFi cells were propagated in Dulbecco's Modified Eagle's Medium (DMEM, Mediatech) and supplemented with 10% fetal bovine serum (Atlanta Biologicals) and 1 mg/mL gentamycin sulfate (Gibco) in a 95% humidity, 5% $CO_2$, 37° C. atmosphere. Cells were seeded as sub-confluent monolayer cultures at a density of $1 \times 10^4$ per well into 96-well, black wall/bottom plates (BD Biosciences) and allowed to adhere for 24 h at 37° C. For evaluation of caspase-3/7 inhibition concomitant with drug exposure, DiFi cells were incubated with cetuximab (0.5 µg/mL) for 24 h, based on our experience from previous work. Cell media was then replaced with 1×PBS containing inhibitor (0, 10, 100, 1000, 10000 nM) and incubated at 37° C. for 30 min. Inhibition was assessed using Caspase-Glo 3/7 reagent in accordance with the manufacturer's instructions. Luminescence was quantified using a Synergy 4 plate reader.

Radiotracer Preparation

Detailed chemical and radiochemical methods and characterization is described below. The radiochemical intermediate [$^{18}$F]N-succinimidyl-4-fluorobenzoate ([$^{18}$F]SFB), was prepared using commercial GE TRACERlab-Synthesizer MX production kits (ABX) with a BIOSCAN Coincidence radiochemistry module. [$^{18}$F]SFB was then conjugated to VAD-FMK forming [$^{18}$F]FB-VAD-FMK.

Animal Model

Studies involving animals were conducted in accordance with federal and institutional guidelines. Biodistribution studies were performed using male C57BL/6 mice. A detailed description of in vitro drug response studies that support the subsequently described animal models and drug therapies is provided below.

Dual xenograft-bearing mice were sequentially injected with $1 \times 10^7$ SW620 and $5 \times 10^6$ DLD-1 human CRC cells subcutaneously onto the left or right hind limbs (respectively) of 5- to 6-week old female, athymic nude mice (Harlan Sprague-Dawley). Palpable tumors were observed 2-3 weeks following inoculation. Animals bearing SW620 and DLD-1 xenograft tumors were treated with vehicle or AZD-1152 (25 mg/kg, DMSO) via intraperitoneal injection once daily for five days, analogous to previous work. In vivo PET imaging studies were performed on Day 5, approximately 4-6 h after treatment.

COLO-205 and LIM-2405 xenografts were generated by subcutaneously injecting $1 \times 10^7$ cells onto the right flank of 5- to 6-week old female, athymic nude mice (Harlan Sprague-Dawley). Palpable tumors were observed within three weeks following inoculation. For BEZ-235 (Selleckchem) and PLX-4720 (synthesized using reported methods) single-agent treatment, animals were administered vehicle, BEZ-235 (35 mg/kg, 0.1% Tween 80 and 0.5% methyl cellulose) or PLX-4720 (60 mg/kg, DMSO) via oral gavage once daily for four days. For BEZ-235 and PLX-4720 combination treatment, BEZ-235 (35 mg/kg, 0.1% Tween 80 and 0.5% methyl cellulose) and PLX-4720 (60 mg/kg, DMSO) were administered via oral gavage as separate doses (respectively) approximately 7-8 h apart. To monitor tumor growth, tumor volumes were measured on Days 1 and 4 of treatment using a previously established ultrasound imaging based methodology. In vivo imaging studies were performed on the $4^{th}$ day (PET), based on our previous experience with BRAF inhibition in vivo.

In Vivo PET Imaging and Analysis

Imaging acquisition and processing was performed analogously to our previously reported methods. Further details are described below.

Immunohistochemistry (IHC)

Tumor tissues were harvested immediately following conclusion of imaging, fixed for 24 h in 5% buffered formalin, and blocked in paraffin. Immunohistochemistry for cleaved caspase-3 (Cell Signaling, #9664) was carried out as previously described. Tissues were stained using standard H&E methods and reviewed by an expert gastrointestinal pathologist (M. Kay Washington). Images displayed are representative of three randomly selected high-power fields (40×). Semi-quantitative IHC analysis was performed using the image processing software ImageJ and is further described below.

Statistical Methods

Unless otherwise stated, experimental replicates are reported as the arithmetic mean±standard deviation. Statistical significance of in vitro and in vivo data sets was evaluated using an unpaired, two-tailed t-test. Differences were assessed within the GraphPad Prism 6.01 software package and considered statistically significant if p<0.05.

Chemicals

Unless otherwise indicated, all chemicals, reagents, and solvents were purchased from Sigma-Aldrich and used as received.

Synthesis of [$^{19}$F]4-Succinimidyl-4-Fluorobenzoate ([$^{19}$F]SFB) (1)

4-[$^{19}$F]Fluorobenzoic acid and N,N,N',N'-tetramethyl-O—(N-succinimidyl)uronium tetrafluoroborate (1:1.5) were combined in a round bottom flask with acetonitrile for a final 4-[$^{19}$F]fluorobenzoic acid concentration of 71.4 mM. Upon reaching the final reaction temperature, 45-50° C., solid tetramethylammonium hydroxide (TMAH, 1.5 eq) was added to the reaction mixture. The reaction vessel was flushed with positive $N_{2(g)}$ pressure and held at this temperature overnight (16-18 h) with stirring. [$^{19}$F]SFB (1) formation was monitored by normal phase thin layer chromatography (TLC) (1:1, ethyl acetate:chloroform, $R_F$=0.76). Purification was performed by flash chromatography with SNAP silica cartridges using an hexanes:ethyl acetate gradient (100% 0-1 min, 100-70% 1-10 min, 70% 10-15 min, 70-30% 15-25 min, 30% 25-35 min; all percentiles with respect to hexanes) on a Biotage flash purification system to give the final, pure product in up to 85% yield. $^1$H-NMR characterization matched that of commercially available authentic compound purchased from Advanced Biochemical Compounds (ABX).

Synthesis of [$^{19}$F]4-fluorobenzylcarbonyl-VAD-FMK ([$^{19}$F]FB-VAD-FMK) (3)

Upon synthesis, (1) was conjugated to VAD-FMK peptide (2) (American Peptide Company) through the N-terminus to form the non-radioactive probe analogue, [$^{19}$F]FB-VAD-FMK (3) (Fig. S2A). Compounds (1) and (2) were reconstituted separately in anhydrous dimethylformamide (DMF) with equimolar amounts of N,N-diisopropylethylamine (DIPEA). Solution (2) was added drop-wise to solution (1) for a final compound (2) concentration of 37.5 mM and final molar equivalencies: 1:2:2 [(1):(2):DIPEA]. The reaction vessel was then flushed with positive $N_{2(g)}$ pressure, heated to 55° C., and held at that temperature overnight (16-18 h) with stirring. Product formation was monitored by TLC [6:4, dichloromethane (DCM):(chloroform:methanol:triethylamine (TEA), 8:1.8:0.2), $R_F$=0.5]. Authentic compound was isolated from free peptide and unconjugated [$^{19}$F]SFB using reversed-phase high-performance liquid chromatography (HPLC) (Varian Dynamax, Microsorb C18, 8 μm, 21.4×250 mm, λ=254 nm). The product eluted between 22-24 min using a phosphate buffer (1 mM):acetonitrile gradient (85% 0-2 min, 85-60% 2-10 min, 60% 10-15 min, 60-30% 15-22 min, 30% 22-40 min; all percentiles with respect to aqueous phase) at a flow rate of 10 mL/min. The final product was rinsed with ethyl acetate and obtained in up to 65% yield.

High-resolution mass spectroscopy (HRMS) was performed using a Waters Synapt Quadrupole Time-of-Flight high-resolution mass spectrometer equipped with a dual channel ESCI ion source. HRMS calculated for $C_{21}H_{28}F_2N_3O_6$ m/z=456.1946 (M)$^+$, found 456.1945. $^1$H, $^{13}$C, and $^{19}$F nuclear magnetic resonance (NMR) spectra were recorded on a Bruker 400 MHz spectrometer. Chemical shifts are reported in ppm using residual DMSO as the internal standard (2.50 ppm for $^1$H, 39.51 ppm for $^{13}$C). The following abbreviations are used for multiplicity of NMR signals: s=singlet, d=doublet, dd=doublet of doublets, t=triplet, q=quartet, sep=septet, m=multiplet. $^1$H-NMR ((CD$_3$)$_2$SO, 400 MHz) δ: 8.62 (d, 1H, J=7.41 Hz), 8.48 (d, 1H, J=7.88 Hz), 8.35-8.27 (m, 2H), 7.94 (m, 2H), 7.28 (t, 2H, J=8.45 Hz), 5.32-5.04 (m, 2H), 4.64 (q, 1H, J=6.90 Hz), 4.48 (q, 1H, J=6.84 Hz), 4.28 (t, 1H, J=8.17 Hz), 4.22-4.12 (m, 1H), 3.59 (s, 3H), 2.86-2.79 (m, 1H), 2.67-2.58 (m, 1H), 2.09 (sep, 1H, J=6.84 Hz), 1.21 (dd, 3H, J=7.08 Hz, J=3.73 Hz), 0.95-0.89 (m, 6H). $^{13}$C-NMR ((CD$_3$)$_2$SO, 400 MHz, $^1$H decoupled) δ: 197.87, 197.73, 197.52, 197.38, 168.54, 168.41, 166.63, 166.57, 166.28, 166.10, 161.07, 161.05, 160.60, 158.13, 125.73, 125.64, 110.65, 110.44, 54.27, 47.76, 47.15, 47.12, 47.01, 44.07, 43.74, 29.51, 29.23, 25.56, 14.65, 14.31, 14.28, 12.82, 12.73. $^{19}$F-NMR ((CD$_3$)$_2$SO, 400 MHz, $^1$H decoupled) δ: −107.36, −230.90, −231.06.

Synthesis of [$^{127}$I]4-iodobenzyl Chloroformate (4)

[$^{127}$I]4-Iodobenzyl alcohol was solubilized in chilled anhydrous dichloromethane (DCM) (0° C.) and added drop-wise to solid triphosgene (1:1) in a reaction vessel under positive $N_{2(g)}$ pressure, with stirring, at 0° C. Final concentration of 44 [$^{127}$I]iodobenzyl alcohol and triphosgene was 674 mM. Reaction mixture was maintained at 0° C. with stirring for 15 min, then brought to room temperature and stirred overnight (16-18 h) protected from light. [$^{127}$I]4-iodobenzyl chloroformate (4) formation was monitored by normal phase TLC (2:8, ethyl acetate:hexanes, $R_F$=0.64). The reaction solvent was removed by rotary evaporation to obtain a mixture of an off-white solid and a brown-colored liquid. The mixture was subsequently washed with hexanes and the liquid phase extracted. Hexanes were removed to obtain (4) as a brown-liquid that was used immediately without further purification.

Synthesis of [$^{127}$I]4-iodobenzyloxycarbonyl-Val-Ala-Asp(OMe)-fluoromethylketone ([$^{127}$I]IZ-VAD-FMK) (5)

[$^{127}$I]IZ-VAD-FMK was synthesized as the para-iodinated regioisomer. Here, (4) was conjugated to (2) to form (5) (Fig. S2B). Compounds (4) and (2) were reconstituted separately in chilled anhydrous DCM (0° C.) with TEA. Solution (4) was added drop-wise to (2) in a reaction vessel under positive $N_{2(g)}$ pressure, with stirring, at 0° C. for a final compound (2) concentration of 60 mM and final molar equivalencies: 4:1:2 [(4):(2):TEA]. The reaction mixture was maintained at 0° C. with stirring for 15 min, then brought to room temperature and subsequently heated at 55° C., with stirring, for 12 h, protected from light. Product formation was monitored by TLC [6:4, DCM:(chloroform: methanol:TEA, 8:1.8:0.2), $R_F$=0.30]. The authentic compound was isolated from free peptide and (4) using HPLC (Varian Dynamax, Microsorb C18, 8 μm, 21.4×250 mm, λ=254 nm). The product eluted between 22-24 min using a phosphate buffer (1 mM):acetonitrile gradient (85% 0-2 min, 85-60% 2-10 min, 60% 10-15 min, 60-30% 15-22 min, 30% 22-40 min; all percentiles with respect to the aqueous phase) at a flow rate of 10 mL/min. The final product was received in approximately 15% yield.

High-resolution mass spectroscopy (HRMS) was performed using a Waters Synapt Quadrupole Time-of-Flight high-resolution mass spectrometer equipped with a dual channel ESCI ion source. HRMS calculated for $C_{22}H_{30}FIN_3O_7$ m/z=594.1113 (M)$^+$, found 594.1107. $^1$H- and $^{13}$C-NMR spectra were recorded on a Bruker 500 MHz spectrometer. Chemical shifts are reported in ppm using residual chloroform as the internal standard (7.26 ppm for $^1$H, 77.36 ppm for $^{13}$C). The following abbreviations are used for multiplicity of NMR signals: s=singlet, br s=broad singlet, d=doublet, t=triplet, m=multiplet. $^1$H-NMR (CDCl$_3$, 500 MHz) δ: 7.69 (d, 2H, J=8.28 Hz), 7.10 (m, 2H), 6.48 (br s, 1H), 5.36 (m, 1H), 5.23-5.18 (m, 1H), 5.13-4.97 (m, 4H), 4.91 (m, 1H), 4.52-4.45 (m, 1H), 3.97 (t, 1H, J=6.82 Hz), 3.68 (s, 3H), 3.13-3.08 (m, 1H), 3.03-2.98 (m, 1), 2.91-2.84 (m, 1), 2.17-2.09 (m, 1H), 1.42-1.37 (m, 4H), 1.25 (s, 2H), 0.98-0.92 (m, 7H). $^{13}$C-NMR (CDCl$_3$, 500 MHz, $^1$H decoupled) δ: 202.56, 172.39, 171.68, 171.62, 156.80, 138.06, 136.05, 130.32, 130.27, 94.33, 85.35, 85.26, 83.89, 83.80, 66.94, 61.00, 52.64, 52.31, 49.33, 35.17, 31.14, 30.05, 19.58, 18.31, 18.10, 8.96.

Analysis of Lipophilicity

Lipophilicity characterization of compounds (3) and (5), as well as Z-VAD-FMK, was performed through log $P_{7.5}$ quantification using methodology analogous to those previously reported (1). Using reversed phase HPLC (Phenomenex Luna C18, 5 μm, 100 Å, 4.6×250 mm) and a (85:15)

phosphate buffer (2 mM, pH 7.5) isocratic system (1 mL/min), log $P_{7.5}$ values were calculated using an average of compound retention times from three individual runs and standard curve derived linear regression. The following standards with known log P values were used for curve development: catechol, aniline, benzene, bromobenze, toluene, ethylbenzene, 2-chlorobiphenyl, biphenyl, 1-chloronaphthalene, 1,2,3-trimethylbenzene, 1,2,3,4-tetrachlorobenzene, 1,2,4,5-tetrabromobenzene, and pentachlorobenzene. Log $P_{7.5}$ values were found to be 1.41, 2.38, and 2.20 for (3), (5), and Z-VAD-FMK, respectively.

Enzyme Selectivity Assay

Relative enzyme inhibition of [$^{19}$F]FB-VAD-FMK was evaluated against caspase-3/6/7/8 using homogeneous caspase fluorescence assay kits (BPS Bioscience) and compared to parent peptide. Caspase inhibitor dissolved in caspase assay buffer and 1% DMSO (0.0003-10 μM) was combined with the caspase assay substrate and enzyme at room temperature for 30 min in accordance with the manufacturer's instructions. Fluorescence intensity was measured at an excitation of 360 nm and an emission of 460 nm using an Infinite M1000 microplate reader (Tecan).

Radiochemical Production of [$^{18}$F]4-fluorobenzylcarbonyl-VAD-FMK ([$^{18}$F]FB-VAD-FMK) (11)

[$^{18}$F]SFB was prepared using commercial GE TRACERlab-Synthesizer MX production kits (ABX) with a BIOSCAN Coincidence radiochemistry module. The automated synthetic route included flourine-18 radiolabeling of 4-[1,1-dimethylethyl ester]-N,N,N-trimethyl-benzenammonium triflate (6) to 4-[$^{18}$F]-1,1-dimethylethyl ester benzoic acid (7), deprotection of to 4-[$^{18}$F]fluorobenzoic acid (8) through alcoholic saponification, and subsequent formation of the activated ester [$^{18}$F]SFB (9) from (8) (Fig. S3A). Radiochemical purity (95±2%) was determined by analytical HPLC (Hitachi High Technologies LaChrom C18, 5 μm, 4.6×150 mm, 1 mL/min, 20-70% acetonitrile:water over 15 min, retention time (RT)=11.5 min, λ=254 nm). [$^{18}$F]SFB was delivered in approximately 3 mL of 4:1 acetonitrile:water, a decay-corrected radiochemical yield of 36±4%, and concentrated to <0.5 mL using positive nitrogen pressure and heating at 55° C. Once concentrated, VAD-FMK (10 mg/mL DMF) and DIPEA (30 μmol) were added to [$^{18}$F]SFB (7.4-13.0 GBq) and heated in a sealed vessel at 55° C. for 45 min (Fig. S3B). [$^{18}$F]FB-VAD-FMK was purified using semi-prep reversed-phase HPLC (Waters Sunfire C18, 5 μm, 10×150 mm) and eluted between 17.7-19 min using a phosphate buffer (1 mM):acetonitrile gradient (85% 0-5 min, 85-60% 5-15 min, 60% 15-25 min, 60-30% 25-45 min; all percentiles in respect to aqueous phase) with a 4 mL/min flow rate. The product fraction was diluted 100-fold with water and passed through a C18 Sep-Pak (Waters). Labeled peptide was eluted with ethanol into a sterile flask and loaded with normal saline (0.9%). Volumes of eluent were modified as needed to ensure a final concentration of 74-185 MBq/mL (1/9, ethanol/saline) with a decay corrected radiochemical yield of 25±7%. [$^{18}$F]SFB conjugation efficiency of crude product (57±5%) and radiochemical purity of final post-prep product (98±1%) were determined using analytical HPLC (Phenomenex Luna C18, 5 μm, 100 Å, 4.6×250 mm) and the following phosphate buffer (1 mM): acetonitrile gradient: 85% 0-2 min, 85-30% 2-10 min, 30% 10-35 min; all percentiles in respect to aqueous phase (flow rate=1 mL/min, RT=12.3 min). Specific activities for [$^{18}$F]SFB (83±56 TBq/mmol) and [$^{18}$F]FB-VAD-FMK (6±3 TBq/mmol) were calculated using an HPLC-derived standard curve.

Cell Cycle Assays

For cell cycle analysis, SW620 and DLD-1 cells were propagated to 50% confluency in 6 cm plates and treated with AZD-1152-hydroxyquinazoline pyrazol anilide (HQPA) (Selleckchem), 0, 10, 100, 1000, or 5000 nM, for 24 or 48 hrs and prepared for flow cytometry as described (2). Propidium iodide (PI)-stained cells were analyzed by flow cytometry (FACStar PLUS, Becton-Dickinson). Data analysis was performed using CellQuest software (Becton-Dickinson) by manually gating to define and quantify sub-G0, G1, S, G2/M, and polyploidy populations. For assay of apoptosis following in vitro AZD-1152-HQPA exposure, SW620 and DLD-1 cells were seeded as sub-confluent monolayer cultures at a density of 1×10$^4$ per well into 96-well, black wall/bottom plates (BD Biosciences), allowed to adhere for 24 h, and treated with AZD-1152-HQPA, 0, 10, 50, 75, 100, or 1,000 nM, for 24 hrs. Apoptosis was assessed using the Caspase-Glo 3/7 reagent, in accordance with manufacturer's instructions, and analyzed using a Synergy 4 plate reader.

Immunoblotting

After 24 h of drug exposure, in vitro cell samples were collected from 10-cm plates. Medium was removed and cell monolayers washed with 1× phosphate buffered saline (PBS) followed by addition of 450 mL of lysis buffer containing: 7 mL of CelLytic M lysis buffer (Sigma), mini protease inhibitor cocktail (Roche), and 100 mL of phosphatase inhibitor cocktail 1 and 2 (Sigma). Protein concentrations were normalized using a bicinchoninic acid assay. All samples were vortexed and centrifuged prior to final cell lysate collection.

Immunoblotting was performed by loading 20-40 μg of protein into 7.5-12% SDS PAGE gels and resolved by electrophoresis. Membranes were incubated with antibodies to cleaved PARP (Cell Signaling, 9541S), cleaved caspase-3 (Cell Signaling, 9664), or GAPDH (Millipore, MAB374) and imaged on a Xenogen IVIS 200 using Western Lightning Plus-ECL (PerkinElmer) substrate.

In Vivo PET Imaging and Analysis

For all imaging studies, mice were maintained under 2% isofluorane anesthesia in 100% oxygen at 2 L/min and kept warm via a circulating water heating pad for the duration of the PET scan. Small-animal PET imaging was performed using a dedicated Concorde Microsystems Focus 220 microPET scanner (Siemens Preclinical Solutions). Animals were administered 7.4-9.3 MBq of [$^{18}$F]FB-VAD-FMK via intravenous injection. Both static and dynamic data sets were acquired. For static scans, animals were allowed free access to food and water during a 20-40 minute uptake period, followed by anesthetization and a 20-minute image acquisition. Analogously, sixty minute dynamic acquisitions for all xenografts were initiated at the time of [$^{18}$F]FB-VAD-FMK injection.

PET data were reconstructed using a three-dimensional (3D) ordered subset expectation maximization/maximum a posteriori (OSEM3D/MAP) algorithm. Dynamic data was binned into twelve 5 s (0-1 min) and fifty-nine 60 s (2-60 min) frames. The resulting three-dimensional reconstructions had an x-y voxel size of 0.474 mm and inter-slice distance of 0.796 mm. ASIPro software (Siemens Preclinical Solutions) was used to manually draw three-dimensional regions of interest (ROI) in the tumor volume. Areas of perceived necrosis were excluded when drawing ROIs. [$^{18}$F]FB-VAD-FMK uptake was quantified as the percentage of the injected dose per gram of tissue (% ID/g); for dynamic scans, only data points collected within the time frame analyzed for analogous static scans were considered.

Semi-Quantitative Analysis

For semi-quantitative analysis of cleaved caspase-3 IHC, the public domain image processing software ImageJ was used to selectively measure the area of positive staining of each cohort through manual threshold manipulation of hue, pixel saturation, and brightness. Analysis was performed for multiple low field (2.5×) tissue micrographs and values reported as the percent area of positive staining over total staining.

Results

Caspase-3 Active Site Accommodates N-Terminal Functionalization of VAD-FMK

Imaging labels should impart minimal, if any, effects upon the biological and chemical properties of the parent molecule. Given this, we initially used a molecular modeling approach to explore multiple N-terminally functionalized analogues of VAD-FMK (FIG. 1A), two of which would result in PET/SPECT imaging probes: FB-VAD-FMK (FIG. 1B), benzyloxycarbonyl-Val-Ala-Asp(OMe)-fluoromethylketone (Z-VAD-FMK), 4-iodobenzyloxycarbonyl-Val-Ala-Asp(OMe)-fluoromethylketone (IZ-VAD-FMK), and VAD-FMK. Molecular docking of each peptide into an irreversible inhibitor bound protein structure of caspase-3 (PDB ID, 3KJF) enabled predictions to be drawn regarding the accommodation of modified peptides into the caspase-3 active site. Flexible docking calculations were performed employing post-docking energy minimization for each peptide to assess potential energetic perturbations that result from N-terminal modification. Only docked poses that positioned the C-terminal fluoro-methyl ketone moiety within 5.0 angstroms of the caspase-3 active site cysteine 163 thiol moiety were considered in our analysis. All four peptides exhibited predicted binding energy scores that fell within the micromolar to nanomolar range (Total Score) and ranked by the steric bump parameter (Crash) using SurflexDock in Tripos SYBYL-X 2.0. See the table, below:

| Compound | Total Score (−log $K_d$) | Crash | Polar | Strain | Similarity |
| --- | --- | --- | --- | --- | --- |
| FB-VAD-FMK | 6.2458 | 0.861 | 5.676 | 0.7802 | 0.2979 |
| Z-VAD-FMK | 8.6257 | 1.004 | 4.776 | 3.0018 | 0.5373 |
| IZ-VAD-FMK | 9.5465 | 1.381 | 4.3824 | 1.4081 | 0.5396 |
| VAD-FMK | 5.1466 | 1.155 | 4.8703 | 2.567 | 0.4582 |

The Surflex-Dock scoring term for Polar contacts suggested that the FB-VAD-FMK peptide had greater potential to form hydrogen bonds with active caspase-3 site residues relative to other candidate structures, including the parent peptide, while displaying less internal ligand Strain scores. Of note, IZ-VAD-FMK produced docking scores that reflected a lower-scoring Polar term and demonstrated that more poses buried the larger, lipophilic iodo-moiety toward the protein active site, suggesting greater lipophilicity than FB-VAD-FMK. Though exploratory in nature, these studies suggested both tolerance to functionalization of VAD-FMK at the N-terminus with the FB prosthesis and that the resulting PET imaging probe might possess favorable physical and chemical properties relative to parent peptide and the IZ-labeled form.

Enzyme Selectivity of VAD-FMK Peptide Analogues

From the binding mechanism of VAD-FMK-type peptides, we anticipated that FB-VAD-FMK would exhibit caspase selectivity similar to that of the parent peptide. To explore this, we evaluated the relative affinity of [$^{19}$F]FB-VAD-FMK against activated caspases-3/6/7/8 (Fig. S1). Addition of the FB-prosthesis had little impact on caspase selectivity compared to that of the parent peptide, where both peptides inhibited caspases-3/6/7 with single micro molar potency and caspase-8 with slightly greater potency. Caspase-3 was used in subsequent characterization and validation studies as a representative of other relevant caspases.

Lipophilicity of VAD-FMK Peptide Analogues

To validate the predicted physical properties of the labeled VAD-FMK derivatives, lipophilicity studies were undertaken using [$^{19}$F]FB-VAD-FMK (Fig. S2A), Z-VAD-FMK, and [$^{127}$I]IZ-VAD-FMK (Fig. S2B). We determined that the FB-modified peptide (log $P_{7.5}$=1.41) was between 50-100 times less lipophilic than both Z-VAD-FMK (log $P_{7.5}$=2.20) and [$^{127}$I]IZ-VAD-FMK (log $P_{7.5}$=2.38), in support of the predicted Polar contact scores determined by molecular modeling. These findings also agree with a previous report of IZ-VAD-FMK, which suggested this compound to be too lipophilic for in vivo use.

[$^{19}$F]FB-VAD-FMK Potently Inhibits Active Caspase Activity

The biological activity of labeled VAD-FMK derivatives was validated with recombinant caspase-3 enzyme using a commercially available chemiluminescent caspase activity assay. Nonlinear regression analysis of the resultant inhibitory profiles yielded a mean (n≥3) fifty-percent inhibitory concentration ($IC_{50}$) of approximately 225±70 nM for [$^{19}$F]FB-VAD-FMK (FIG. 1C). Though all peptides exhibited reasonable potencies that were in line with predicted affinities, [$^{19}$F]FB-VAD-FMK demonstrated the greatest potency towards caspase-3 inhibition. Similar to biochemical analysis, [$^{19}$F]FB-VAD-FMK inhibited caspase-3/7 activity at nanomolar concentrations analogously to the parent in CRC cells (DiFi) in log-phase growth (FIG. 1D, E). When apoptosis was induced in DiFi cells by exposure to the EGFR monoclonal antibody cetuximab, [$^{19}$F]FB-VAD-FMK inhibited caspase-3/7 activity with comparable efficacy to the parent peptide. Combined with studies demonstrating acceptable physical properties, these investigations illustrated that [$^{19}$F]FB-VAD-FMK exhibited caspase affinity similar to the parent VAD-FMK peptide and was subsequently prioritized for radiochemical development.

In Vivo Normal Tissue Uptake of [$^{18}$F]FB-VAD-FMK

Figure 2:
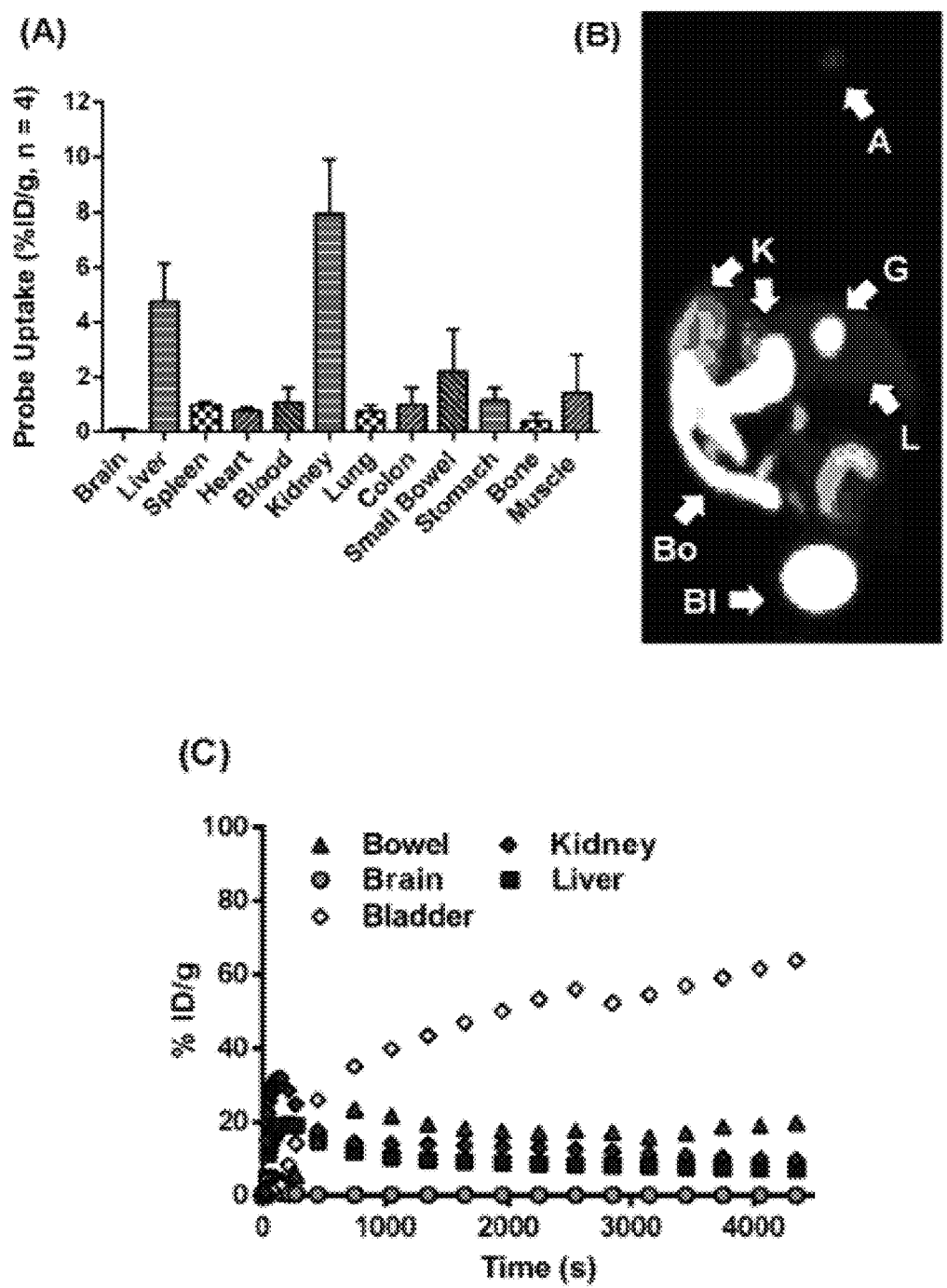
FIG. 2. In vivo biodistribution of [$^{19}$F]FB-VAD-FMK in normal tissue. Probe biodistribution as assessed from ex vivo tissue count studies in male C57BL/6 mice (n=4) (A), and a representative PET imaged maximum intensity projection (MIP) (B), A=administration site, Bl=bladder, Bo=bowel, G=gallbladder, K=kidney, L=liver, and corresponding time-activity curves (C) for normal tissues of a non-tumor bearing athymic nude mouse.

Radiochemical preparation of [$^{18}$F]FB-VAD-FMK (Fig. S3) was performed as described above. The in vivo biodistribution of [$^{18}$F]FB-VAD-FMK was evaluated by ex vivo tissue counting at 60 min post-administration and correlative PET imaging up to 75 min post-administration. Upon intravenous administration, [$^{18}$F]FB-VAD-FMK was widely distributed throughout a range of normal tissues, with the greatest activity in kidneys and liver after 60 minutes of uptake (FIG. 2A). Very little radioactivity was found in brain, lung, or bone. Summed dynamic PET acquisitions following [$^{18}$F]FB-VAD-FMK administration, 0-75 min (FIG. 2B, C), agreed with tissue counting measurements and provided evidence of renal and hepatobiliary excretion. This was confirmed by HPLC radiometabolite analysis, using a protocol analogous to that described in supporting information (SI) for radiochemical purity analysis, which revealed largely parent compound, approximately 50% or greater, in bile and urine samples (n=3) at 60 min post injection.

Figure 3:
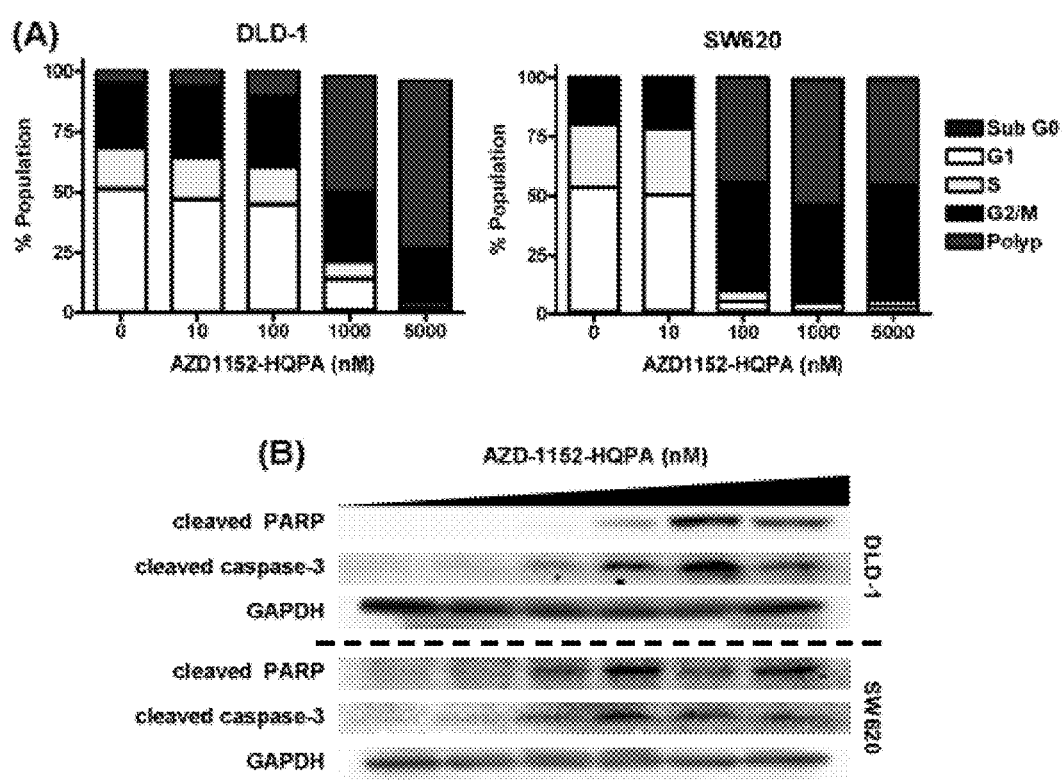
FIG. 3. AZD-1152-HQPA in vitro exposure results in cell death in DLD-1 and SW620 cell lines. Cell cycle analysis by PI flow cytometry (A), caspase-3/7 activity (n=5) (B), and western blot analysis of cleaved PARP and cleaved caspase-3 (C) 24 h post drug administration. Drug concentrations for western blotting were: 0, 10, 100, 500, 1000, or 5000 nM.

[$^{18}$F]FB-VAD-FMK PET Reflects AZD-1152-Dependent Caspase-3 Activity in Tumors In vivo uptake of [$^{18}$F]FB-VAD-FMK in tumor was evaluated in SW620 and DLD-1 human CRC cell line xenografts given the in vitro data which demonstrated, in concert with polyploidy (FIG. 3A), AZD-1152-HQPA concentration-dependent increases in cleaved PARP and cleaved caspase-3 levels (FIG. 3B). These results, in addition to previously reported in vivo findings, suggest that quantification of caspase activity may reflect response to Aurora B kinase inhibition in these models.

Figure 4:
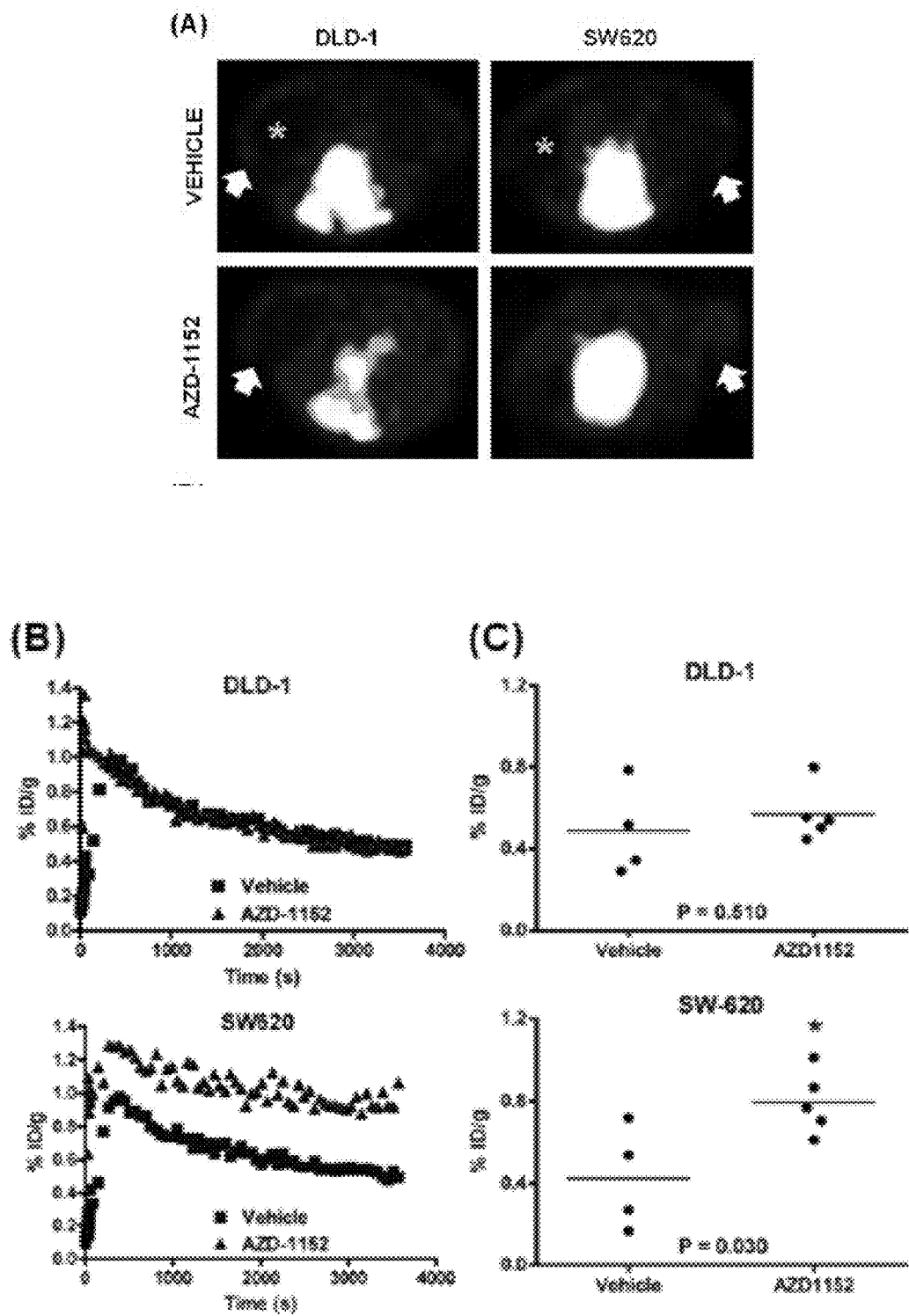
FIG. 4. [$^{18}$F]FB-VAD-FMK uptake reflects molecular response to Aurora B kinase inhibition in vivo. Representative [$^{18}$F]FB-VAD-FMK transverse PET images of DLD-1/SW620 xenograft-bearing mice treated with vehicle or AZD-1152; tumors denoted by white arrows. Probe accumulation was absent in areas of central necrosis, as denoted by orange asterisks (A). Representative [$^{18}$F]FB-VAD-FMK time-activity curves for vehicle- and drug-treated DLD-1 and SW620 xenograft tumors. Vehicle- and drug-treated DLD-1 tumors exhibited similar washout, while greater retention in drug-versus vehicle-treated xenografts was observed for SW620 tumors (B). Quantification of tissue % ID/g revealed a statistical significant difference between vehicle- and drug-treated SW620 (p=0.030) tumors but not for analogously treated DLD-1 tumors (p=0.510) (C). Representative high-power white-light photo micrographs (40×) of caspase-3 immunohistochemical and H&E stained DLD-1 and SW620 tissues obtained from xenografts collected immediately following imaging (D).

In vivo [$^{18}$F]FB-VAD-FMK PET was explored as a means to reflect response to AZD-1152 compared to vehicle. Animals were treated for five days and subjected to imaging after treatment on the fifth day. While vehicle treatment did not result in significant accumulation of [$^{18}$F]FB-VAD-FMK in either xenograft model, AZD-1152 treatment increased [$^{18}$F]FB-VAD-FMK uptake relative to vehicle in SW620 xenografts (0.79±0.15% ID/g and 0.42±0.25% ID/g respectively, p=0.030) (FIG. 4A-C), which was in agreement with in vitro studies. Interestingly, [$^{18}$F]FB-VAD-FMK uptake was absent in areas of central necrosis, as evident from 3D PET images (FIG. 4A). Interestingly, unlike in vitro studies that illustrated the sensitivity of DLD-1 cells to AZD-1152, probe accumulation was similar between AZD-1152-treated and vehicle-treated DLD-1 xenografts (0.57±0.14% ID/g and 0.49±0.22% ID/g respectively, p=0.510).

To validate imaging, xenograft tissues were harvested for histology immediately following imaging. In agreement with [$^{18}$F]FB-VAD-FMK PET, caspase-3 immunoreactivity appeared modest in both vehicle-treated SW620 and DLD-1 xenografts (FIG. 4D). Furthermore, AZD-1152 treatment led to elevated caspase-3 immunoreactivity compared to vehicle-treatment in SW620 but not DLD-1 xenografts as verified with semi-quantitative IHC analysis (Fig. S4A). AZD-1152-treated SW620 xenografts demonstrated evidence of drug exposure given the presence of enlarged nuclei evident by hematoxylin and eosin (H&E) staining. Conversely, the lack of in vivo effects of AZD-1152 in DLD-1 xenografts, predicted by [$^{18}$F]FB-VAD-FMK PET, could possibly be attributed to poor drug exposure as little evidence of polyploidy was observed by H&E staining (FIG. 4D).

[$^{18}$F]FB-VAD-FMK PET Reflects Response to Combination Therapy

Figure 5:
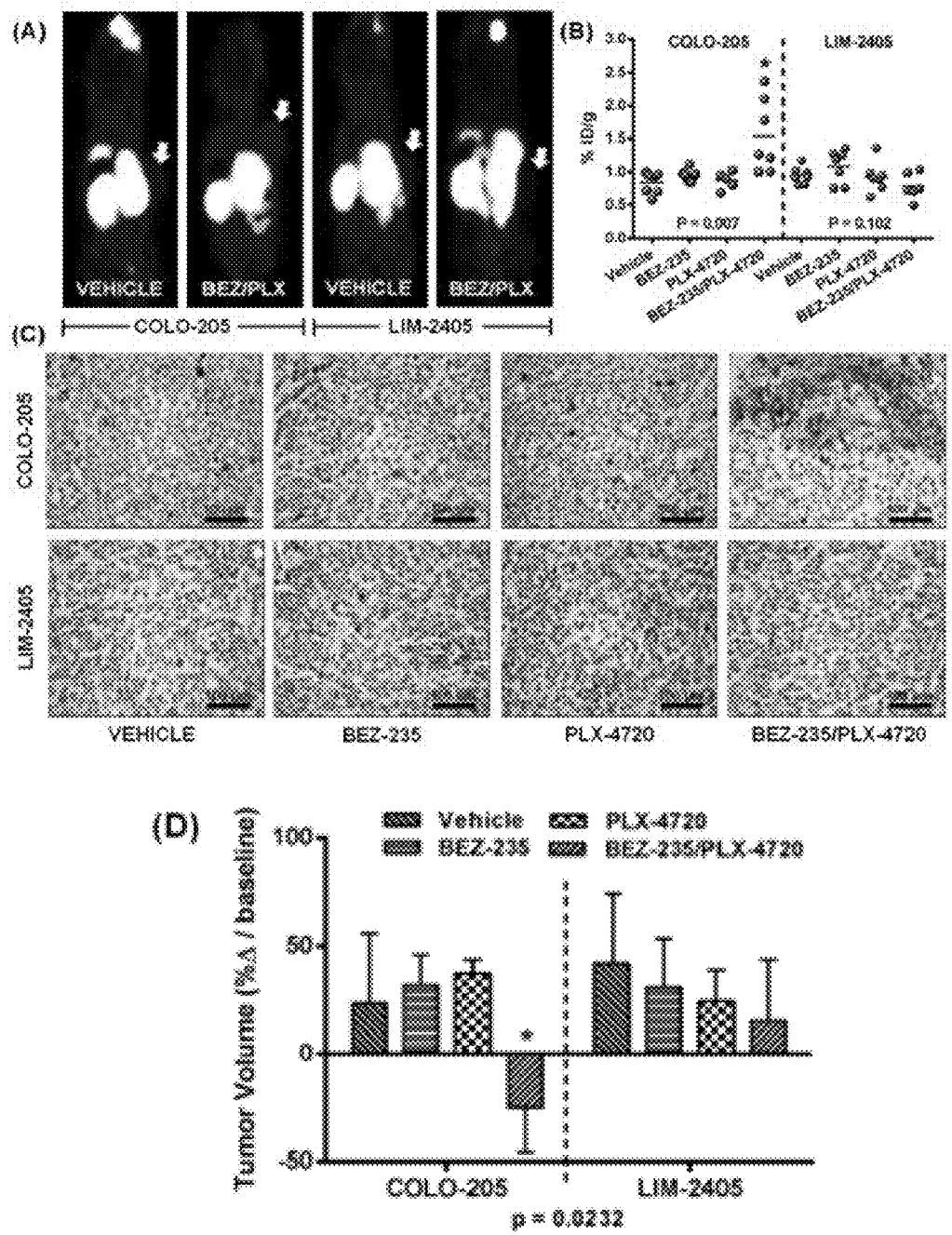
FIG. 5. [$^{18}$F]FB-VAD-FMK uptake reflects molecular response to combination therapy in vivo. Representative [$^{18}$F]FB-VAD-FMK coronal PET images of COLO-205 and LIM-2405 xenograft tumor-bearing vehicle or BEZ-235/PLX-4720-treated mice. Tumors are denoted by white arrows (A). PET quantification of tissue % ID/g revealed a significant difference between vehicle and BEZ-235/PLX-4720-treated COLO-205 (p=0.007) xenografts but not for analogously treated LIM-2405 xenografts (p=0.102) (B). Representative high-power white-light photo micrographs (40×) of caspase-3 immunohistochemical stained COLO-205 and LIM-2405 tissues obtained from xenografts collected immediately following imaging (C). Changes in COLO-205 and LIM-2405 tumor volumes by Day 4 of treatment, shown as percent change from Day 1 baseline, revealed a significant difference compared to vehicle-treated mice (p=0.023) for BEZ-235/PLX-4720-treated COLO-205 tumors only (D).
Figure 6:
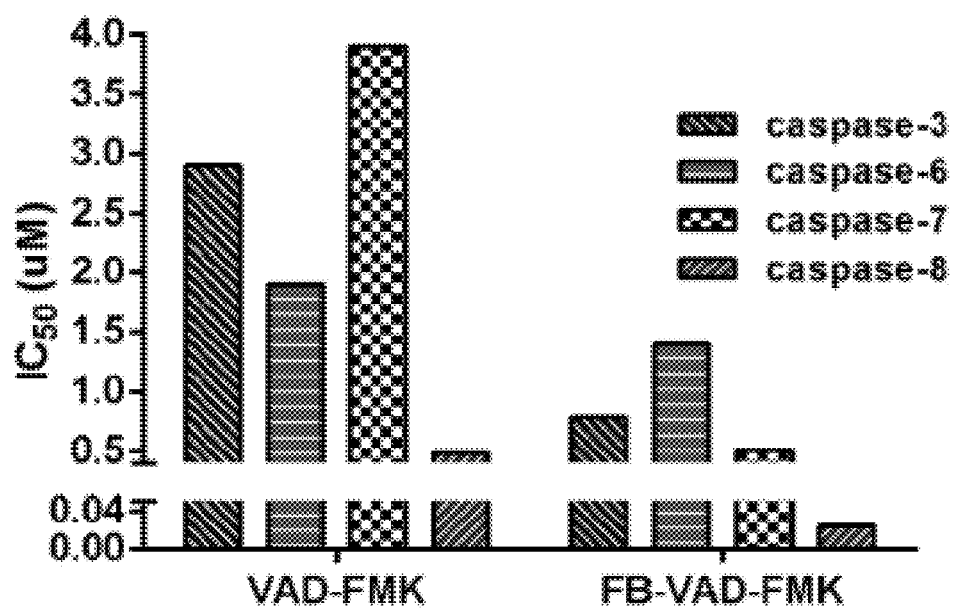
FIG. 6 is a table that shows relative affinity of [$^{19}$F]FB-VAD-FMK against activated caspases-3/6/7/8.
Figure 7:
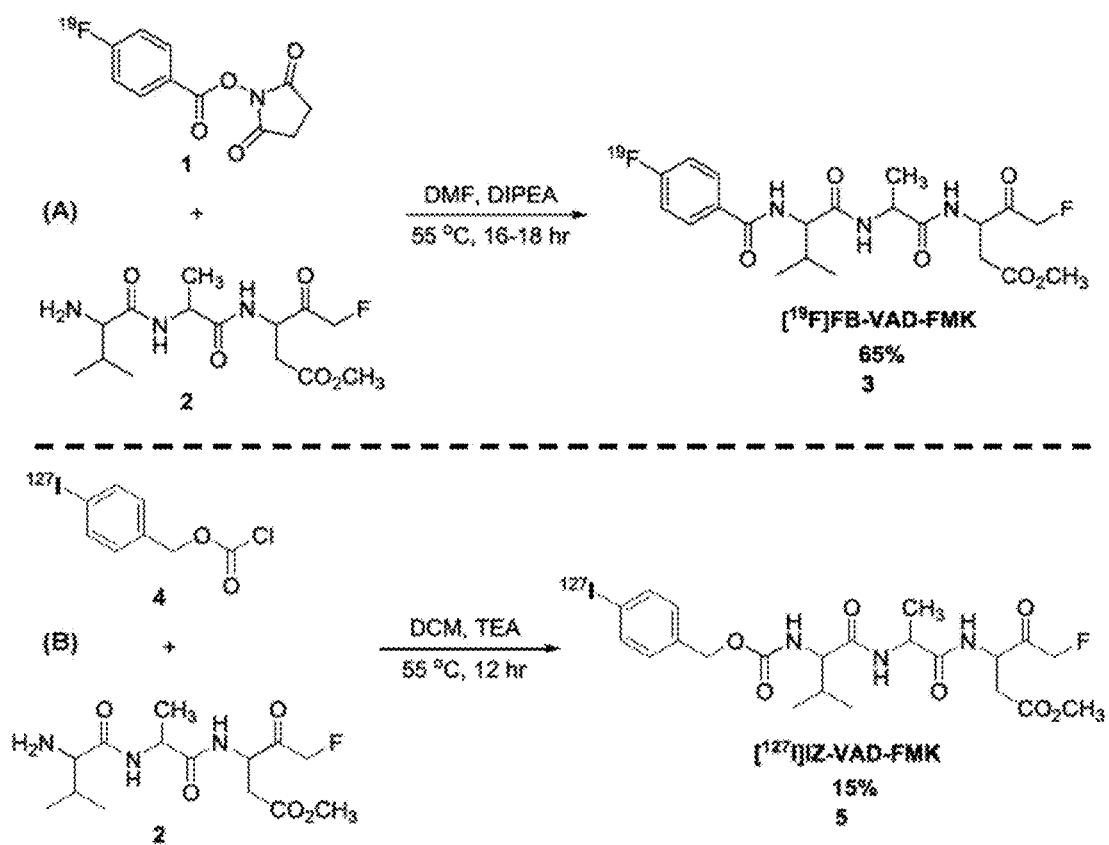
FIGS. 7 and 8 show examples of schemes to make embodiments of the present invention.
Figure 8:
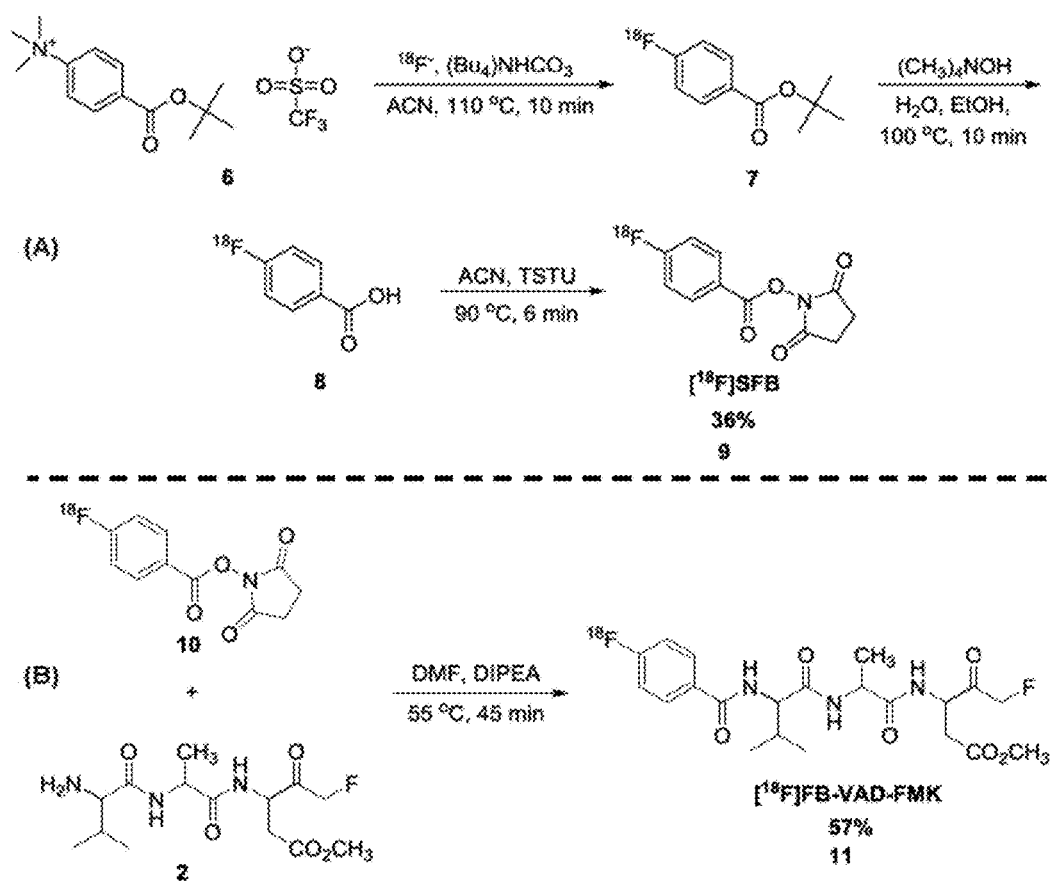
Figure 9:
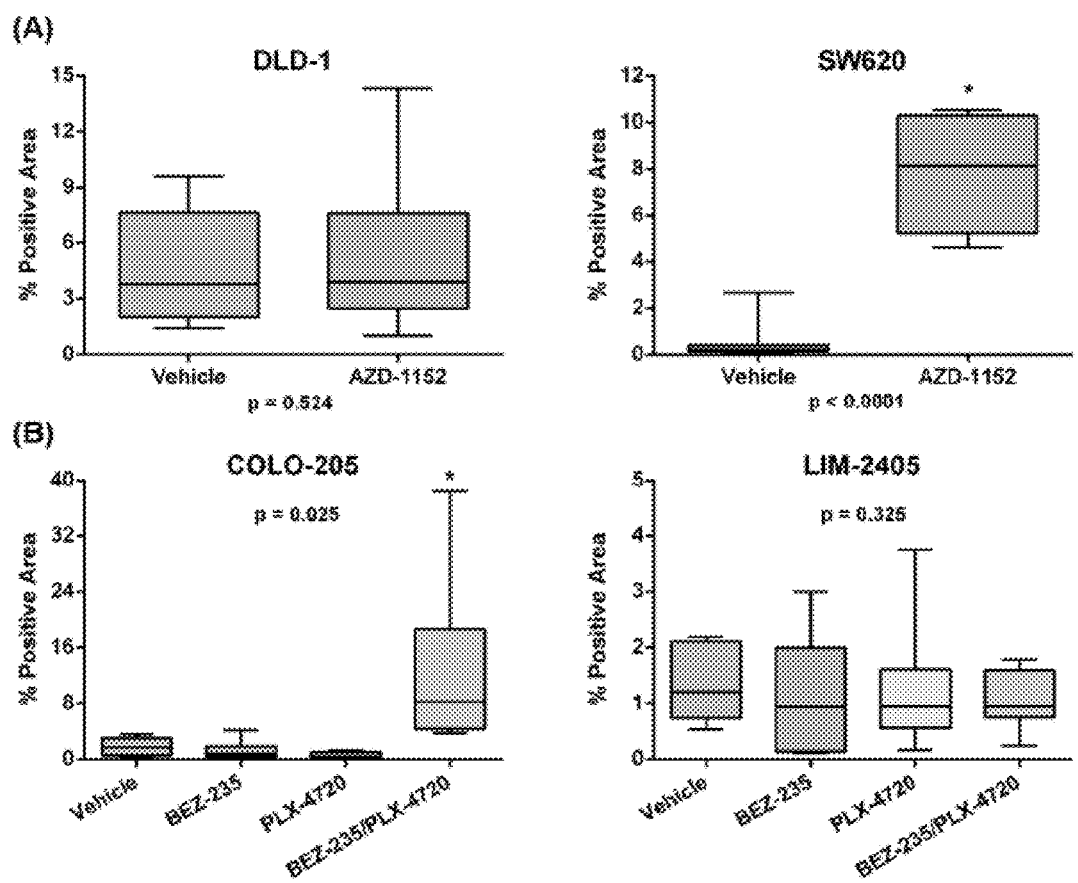
FIG. 9 is a set of tables showing AZD-1152 treatment led to elevated caspase-3 immunoreactivity compared to vehicle-treatment in SW620 but not DLD-1 xenografts as verified with semi-quantitative IHC analysis.

Rational combination therapy for $^{V600E}$BRAF melanoma and colon cancer include an inhibitor of mutant BRAF and a PI3K family inhibitor. Leveraging this concept, [$^{18}$F]FB-VAD-FMK uptake was evaluated in $^{V600E}$BRAF-expressing CRC xenograft-bearing mice (COLO-205 and LIM-2405) treated with vehicle, single-agent PI3K/mTOR inhibitor (BEZ-235), single-agent BRAF inhibitor (PLX-4720), or combination therapy (BEZ-235/PLX-4720). Animals were imaged by PET after treatment on Day 4. Elevated probe uptake in COLO-205 xenografts, relative to vehicle treatment (0.84±0.16% ID/g), was observed in the dual-agent-treated cohort (1.54±0.55% ID/g, p=0.007) but not for either the BEZ-235 or PLX-4720 single agent cohorts (0.94±0.09% ID/g, p=0.14 and 0.87±0.13% ID/g, p=0.69, respectively) (FIG. 5A, B). Strikingly, probe uptake in LIM-2405 xenografts was non-differential, relative to vehicle treatment (0.95±0.13% ID/g), across treatment cohorts: 1.08±0.25% ID/g, p=0.22 (BEZ-235), 0.92±0.23% ID/g, p=0.81 (PLX-4720), and 0.78±0.20% ID/g, p=0.10 (BEZ-235/PLX-4720). Representative xenograft tissue was harvested immediately following imaging. In agreement with [$^{18}$F]FB-VAD-FMK PET, caspase-3 immunoreactivity appeared modest in vehicle- and single-agent-treated COLO-205 and LIM-2405 xenografts, while combination treatment increased caspase-3 immunoreactivity in COLO-205 but not LIM-2405 xenografts (FIG. 5C). These observations were confirmed with semi-quantitative IHC analysis (Fig. S4B). In concert with elevated probe uptake, after four days of treatment a significant reduction in tumor size (p=0.023) was observed in COLO-205 xenografts treated with combination therapy (FIG. 5D). In contrast, statistically significant changes in tumor growth compared to vehicle were not found for single agent therapies in COLO-205 xenografts or any drug therapies in LIM-2405 cohorts Discussion Irreversible caspase binding ligands are frequently utilized as tool compound inhibitors in vitro and in vivo. Among the known inhibitors, we sought to extend the utility of VAD-FMK-type peptides to PET imaging probe development. Mechanistically, VAD-FMK peptides irreversibly bind active caspase through condensation of the fluoromethyl ketone moiety with a cysteine thiol, Cys163 for caspase-3, within the active site, permanently inactivating the enzyme. As a molecular imaging probe, irreversible binding may confer certain advantages, such as enhanced retention in apoptotic versus healthy cells, due to slow dissociation kinetics. We believe this study is the first to report development and in vivo validation of a novel PET imaging probe derived from the VAD-FMK peptide sequence. In general, the VAD-FMK sequence is known to be quite versatile and has been previously functionalized with fluorophores and a radioisotope for in vitro and certain preclinical applications. The probe developed here possesses all of the inherent advantages of a PET imaging agent, which include sensitivity, depth, and quantification. Furthermore, the FB derivative exhibits certain physical properties, such as improved water solubility which was a previously reported limitation of another reported labeled peptide IZ-VAD-FMK.

Using established radiochemical methods, [$^{18}$F]FB-VAD-FMK was produced with activity and purity suitable for use in small animal PET imaging studies. [$^{18}$F]FB-VAD-FMK was initially evaluated in vivo in two CRC cell line models (SW620 and DLD-1) in response to prodrug (AZD-1152) treatment. Upon conversion to the active form of AZD-1152-HQPA in plasma, AZD-1152-HQPA inhibits Aurora B kinase activity and induces 4N DNA accumulation, endoreduplication, and polyploidy. As demonstrated here and elsewhere, these events lead to apoptosis-induced cell death and elevated caspase activity in SW620 tumor cells. The present inventors discovered that [$^{18}$F]FB-VAD-FMK PET could be used to monitor response in this setting and that imaging accurately reflected elevated levels of apoptosis in prodrug-versus vehicle-treated tumors and was validated by immunohistochemistry analysis. Caspase-3 activity corresponded accordingly with evidence of drug exposure as determined by tumor polyploidic events in tissue. Interestingly, in DLD-1 xenografts, [$^{18}$F]FB-VAD-FMK uptake was not differential between drug-treated and vehicle-treated tumors. Tissues collected from these animals agreed with these findings and revealed little evidence of drug activity, as noted by the absence of polyploidy and caspase-3 activity. Thus, in this model, [$^{18}$F]FB-VAD-FMK PET quantization reflected a lack of efficacy that appeared to be the result of poor therapeutic delivery.

Next, [$^{18}$F]FB-VAD-FMK PET was used to evaluate response to a multi-drug therapeutic regimen, which included an inhibitor of mutant BRAF and a PI3K/mTOR inhibitor in $^{V600E}$BRAF-expressing CRC models. A non-invasive imaging metric that can be used to elucidate the basis of response to complicated therapeutic multidrug regimens would be very attractive within the setting of drug development clinical trials. [$^{18}$F]FB-VAD-FMK PET imaging demonstrated that combination therapy led to elevated apoptosis in one of two models compared to vehicle-treated or single-agent-treated CRC xenograft bearing mice. It was found that changes in tumor growth closely correlated with levels of caspase activity detected by both [$^{18}$F]FB-VAD-FMK PET and IHC analysis.

Embodiments of the present invention show that caspase-specific PET imaging probes, such as [$^{18}$F]FB-VAD-FMK, are beneficial in the assessment of early clinical response to therapeutics.

REFERENCES

Throughout this application, various publications are referenced. All such publications, specifically including the publications listed below, are incorporated herein by reference in their entirety.

1. Bosman F T, Visser B C, van Oeveren J. Apoptosis: pathophysiology of programmed cell death. Pathol Res Pract. 1996; 192:676-83.
2. Duprez L, Wirawan E, Vanden Berghe T, Vandenabeele P. Major cell death pathways at a glance. Microbes Infect. 2009; 11:1050-62.
3. Hanahan D, Weinberg R A. Hallmarks of cancer: the next generation. Cell. 2011; 144:646-74.
4. Chang J, Ormerod M, Powles T J, Allred D C, Ashley S E, Dowsett M. Apoptosis and proliferation as predictors of chemotherapy response in patients with breast carcinoma. Cancer. 2000; 89:2145-52.
5. Cotter T G. Apoptosis and cancer: the genesis of a research field. Nat Rev Cancer. 2009; 9:501-7.
6. Reshef A, Shirvan A, Akselrod-Ballin A, Wall A, Ziv I. Small-molecule biomarkers for clinical PET imaging of apoptosis. J Nucl Med. 2010; 51:837-40.
7. Boersma H H, Kietselaer B L, Stolk L M, Bennaghmouch A, Hofstra L, Narula J, et al. Past, present, and future of annexin A5: from protein discovery to clinical applications. J Nucl Med. 2005; 46:2035-50.
8. Nguyen Q D, Challapalli A, Smith G, Fortt R, Aboagye E O. Imaging apoptosis with positron emission tomography: 'bench to bedside' development of the caspase-3/7 specific radiotracer [(18)F]ICMT-11. Eur J Cancer. 2012; 48:432-40.
9. Manning H C, Merchant N B, Foutch A C, Virostko J M, Wyatt S K, Shah C, et al. Molecular imaging of therapeutic response to epidermal growth factor receptor blockade in colorectal cancer. Clin Cancer Res. 2008; 14:7413-22.
10. Shah C, Miller T W, Wyatt S K, McKinley E T, Olivares M G, Sanchez V, et al. Imaging biomarkers predict response to anti-HER2 (ErbB2) therapy in preclinical models of breast cancer. Clin Cancer Res. 2009; 15:4712-21.
11. Schutters K, Reutelingsperger C. Phosphatidylserine targeting for diagnosis and treatment of human diseases. Apoptosis. 2010; 15:1072-82.
12. Blankenberg F G, Vanderheyden J L, Strauss H W, Tait J F. Radiolabeling of HYNIC-annexin V with technetium-99m for in vivo imaging of apoptosis. Nat Protoc. 2006; 1:108-10.
13. Ke S, Wen X, Wu Q P, Wallace S, Charnsangavej C, Stachowiak A M, et al. Imaging taxane-induced tumor apoptosis using PEGylated, 111In-labeled annexin V. J Nucl Med. 2004; 45:108-15.
14. Yagle K J, Eary J F, Tait J F, Grierson J R, Link J M, Lewellen B, et al. Evaluation of 18F-annexin V as a PET imaging agent in an animal model of apoptosis. J Nucl Med. 2005; 46:658-66.
15. Bauwens M, De Saint-Hubert M, Devos E, Deckers N, Reutelingsperger C, Mortelmans L, et al. Site-specific 68Ga-labeled Annexin A5 as a PET imaging agent for apoptosis. Nucl Med Biol. 2011; 38:381-92.
16. Balasubramanian K, Mirnikjoo B, Schroit A J. Regulated externalization of phosphatidylserine at the cell surface: implications for apoptosis. J Biol Chem. 2007; 282: 18357-64.
17. Dillon S R, Constantinescu A, Schlissel M S. Annexin V binds to positively selected B cells. J Immunol. 2001; 166:58-71.
18. Balasubramanian K, Schroit A J. Aminophospholipid asymmetry: A matter of life and death. Annu Rev Physiol. 2003; 65:701-34.
19. Elliott J I, Surprenant A, Marelli-Berg F M, Cooper J C, Cassady-Cain R L, Wooding C, et al. Membrane phosphatidylserine distribution as a non-apoptotic signalling mechanism in lymphocytes. Nat Cell Biol. 2005; 7:808-16.
20. Hoglund J, Shirvan A, Antoni G, Gustaysson S A, Langstrom B, Ringheim A, et al. 18F-ML-10, a PET tracer for apoptosis: first human study. J Nucl Med. 2011; 52:720-5.
21. Allen A M, Ben-Ami M, Reshef A, Steinmetz A, Kundel Y, Inbar E, et al. Assessment of response of brain metastases to radiotherapy by PET imaging of apoptosis with (1)(8)F-ML-10. Eur J Nucl Med Mol Imaging. 2012; 39:1400-8.
22. Blankenberg F G. In vivo detection of apoptosis. J Nucl Med. 2008; 49 Suppl 2:81S-95S.
23. Garcia-Calvo M, Peterson E P, Leiting B, Ruel R, Nicholson D W, Thornberry N A. Inhibition of human caspases by peptide-based and macromolecular inhibitors. J Biol Chem. 1998; 273:32608-13.
24. Ekert P G, Silke J, Vaux D L. Caspase inhibitors. Cell Death Differ. 1999; 6:1081-6.
25. Ganesan R, Jelakovic S, Campbell A J, Li Z Z, Asgian J L, Powers J C, et al. Exploring the S4 and 51 prime subsite specificities in caspase-3 with aza-peptide epoxide inhibitors. Biochemistry. 2006; 45:9059-67.
26. Wang Z, Watt W, Brooks N A, Harris M S, Urban J, Boatman D, et al. Kinetic and structural characterization of caspase-3 and caspase-8 inhibition by a novel class of irreversible inhibitors. Biochim Biophys Acta. 2010; 1804:1817-31.
27. Waterhouse R N, Mardon K, Giles K M, Collier T L, O'Brien J C. Halogenated 4-(phenoxymethyl)piperidines as potential radiolabeled probes for sigma-1 receptors: in vivo evaluation of [1231]-1-(iodopropen-2-yl)-4-[(4-cyanophenoxy)methyl]pip eri dine. J Med Chem. 1997; 40:1657-67.
28. Ren Y G, Wagner K W, Knee D A, Aza-Blanc P, Nasoff M, Deveraux Q L. Differential regulation of the TRAIL death receptors DR4 and DR5 by the signal recognition particle. Mol Biol Cell. 2004; 15:5064-74.
29. Xu J, Li K, Smith R A, Waterton J C, Zhao P, Chen H, et al. Characterizing tumor response to chemotherapy at various length scales using temporal diffusion spectroscopy. PLoS One. 2012; 7:e41714.
30. Buck J R, Saleh S, Uddin M I, Manning H C. Rapid, Microwave-Assisted Organic Synthesis of Selective (V600E)BRAF Inhibitors for Preclinical Cancer Research. Tetrahedron Lett. 2012; 53:4161-5.
31. Ayers G D, McKinley E T, Zhao P, Fritz J M, Metry R E, Deal B C, et al. Volume of preclinical xenograft tumors is more accurately assessed by ultrasound imaging than manual caliper measurements. J Ultrasound Med. 2010; 29:891-901.
32. McKinley E T, Smith R A, Zhao P, Fu A, Saleh S A, Uddin M I, et al. 3'-Deoxy-3'-18F-fluorothymidine PET predicts response to (V600E)BRAF-targeted therapy in preclinical models of colorectal cancer. J Nucl Med. 2013; 54:424-30.
33. Haberkorn U, Kinscherf R, Krammer P H, Mier W, Eisenhut M. Investigation of a potential scintigraphic marker of apoptosis: radioiodinated Z-Val-Ala-DL-Asp (O-methyl)-fluoromethyl ketone. Nucl Med Biol. 2001; 28:793-8.
34. Pereira N A, Song Z. Some commonly used caspase substrates and inhibitors lack the specificity required to monitor individual caspase activity. Biochem Biophys Res Commun. 2008; 377:873-7.
35. Wilkinson R W, Odedra R, Heaton S P, Wedge S R, Keen N J, Crafter C, et al. AZD1152, a selective inhibitor of Aurora B kinase, inhibits human tumor xenograft growth by inducing apoptosis. Clin Cancer Res. 2007; 13:3682-8.
36. Tsai J, Lee J T, Wang W, Zhang J, Cho H, Mamo S, et al. Discovery of a selective inhibitor of oncogenic B-Raf kinase with potent antimelanoma activity. Proc Natl Acad Sci USA. 2008; 105:3041-6.
37. Bollag G, Hirth P, Tsai J, Zhang J, Ibrahim P N, Cho H, et al. Clinical efficacy of a RAF inhibitor needs broad target blockade in BRAF-mutant melanoma. Nature. 2010; 467:596-9.
38. Rauber P, Angliker H, Walker B, Shaw E. The synthesis of peptidylfluoromethanes and their properties as inhibitors of serine proteinases and cysteine proteinases. Biochem J. 1986; 239:633-40.
39. Bedner E, Smolewski P, Amstad P, Darzynkiewicz Z. Activation of caspases measured in situ by binding of fluorochrome-labeled inhibitors of caspases (FLICA): correlation with DNA fragmentation. Exp Cell Res. 2000; 259:308-13.
40. Amstad P A, Yu G, Johnson G L, Lee B W, Dhawan S, Phelps D J. Detection of caspase activation in situ by fluorochrome-labeled caspase inhibitors. Biotechniques. 2001; 31:608-10, 12, 14, passim.
41. Smolewski P, Bedner E, Du L, Hsieh T C, Wu J M, Phelps D J, et al. Detection of caspases activation by fluorochrome-labeled inhibitors: Multiparameter analysis by laser scanning cytometry. Cytometry. 2001; 44:73-82.
42. Lawson V A, Haigh C L, Roberts B, Kenche V B, Klemm H M, Masters C L, et al. Near-infrared fluorescence imaging of apoptotic neuronal cell death in a live animal model of prion disease. ACS Chem Neurosci. 2010; 1:720-7.
43. Peterson T E, Manning H C. Molecular imaging: 18F-FDG PET and a whole lot more. J Nucl Med Technol. 2009; 37:151-61.
44. Eckelman W C, Reba R C, Kelloff G J. Targeted imaging: an important biomarker for understanding disease progression in the era of personalized medicine. Drug Discov Today. 2008; 13:748-59.
45. Mortlock A A, Foote K M, Heron N M, Jung F H, Pasquet G, Lohmann J J, et al. Discovery, synthesis, and in vivo activity of a new class of pyrazoloquinazolines as selective inhibitors of aurora B kinase. J Med Chem. 2007; 50:2213-24.
46. Nguyen Q D, Smith G, Glaser M, Perumal M, Arstad E, Aboagye E O. Positron emission tomography imaging of drug-induced tumor apoptosis with a caspase-3/7 specific [18F]-labeled isatin sulfonamide. Proc Natl Acad Sci USA. 2009; 106:16375-80.
47. Chen D L, Zhou D, Chu W, Herrbrich P E, Jones L A, Rothfuss J M, et al. Comparison of radiolabeled isatin analogs for imaging apoptosis with positron emission tomography. Nucl Med Biol. 2009; 36:651-8.
48. Chen D L, Zhou D, Chu W, Herrbrich P, Engle J T, Griffin E, et al. Radiolabeled isatin binding to caspase-3 activation induced by anti-Fas antibody. Nucl Med Biol. 2012; 39:137-44.
49. Su H, Chen G, Gangadharmath U, Gomez L F, Liang Q, Mu F, et al. Evaluation of [(18)F]-CP18 as a PET imaging tracer for apoptosis. Mol Imaging Biol. 2013; 15:739-47.
50. Xia C F, Chen G, Gangadharmath U, Gomez L F, Liang Q, Mu F, et al. In vitro and in vivo evaluation of the caspase-3 substrate-based radiotracer [(18)F]-CP18 for PET imaging of apoptosis in tumors. Mol Imaging Biol. 2013; 15:748-57.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

We claim:

1. A method of imaging a molecular event in a sample, comprising:
   (a) administering to said sample a probe having an affinity for a target, the probe comprising a compound of the following:

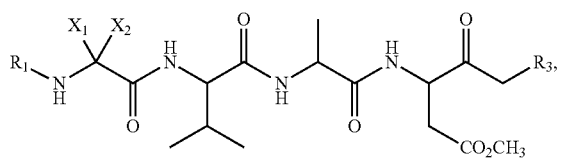

wherein:
  $R_1$ is selected from
  (i) alkyl-halogen, CO-alkyl-halogen, CO-phenyl, CO-alkyl-phenyl, CO-pyridinyl, wherein alkyl is optionally substituted with one or more $R_7$, and phenyl or pyridinyl is optionally halogen-substituted;

(ii)

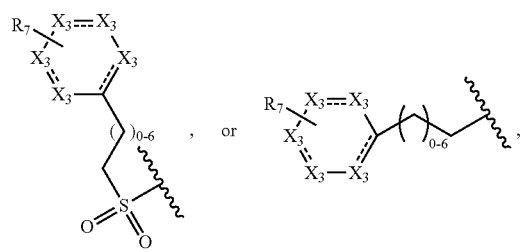

(iii)

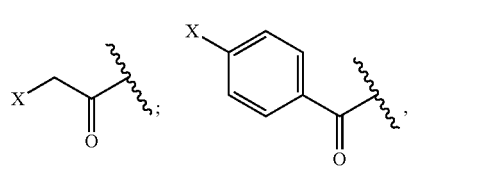

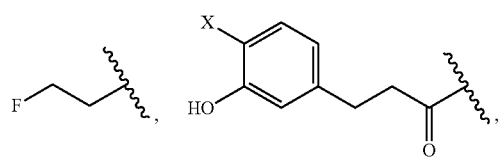

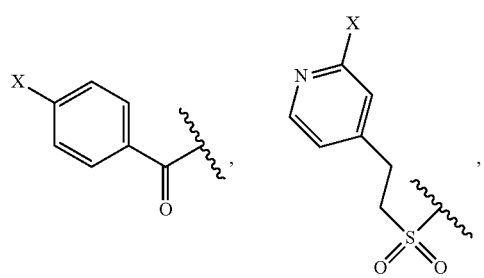

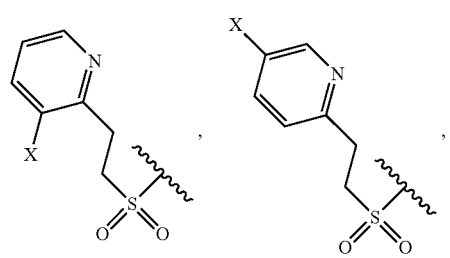

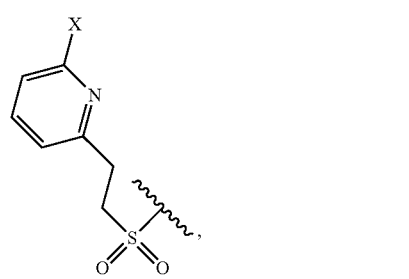

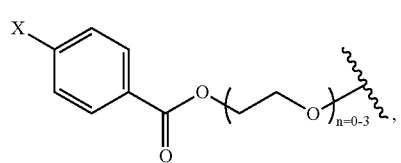

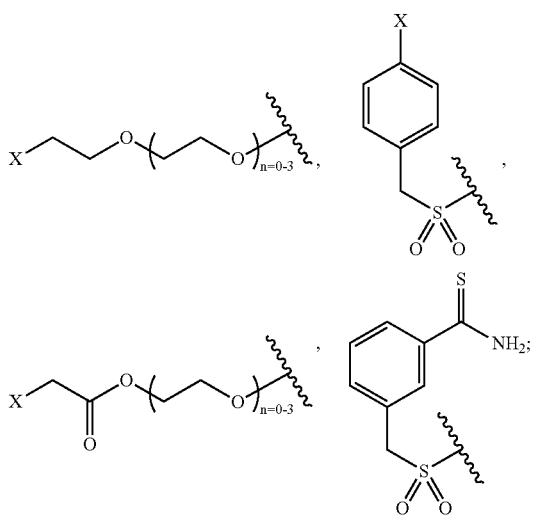

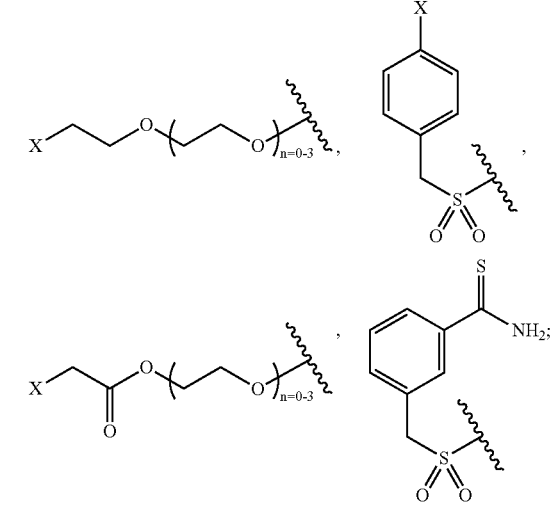

X is iodine or fluorine;

$R_3$ is halogen;

$R_5$ is selected from alkyl, alkoxy;

$R_7$ is selected from hydrogen, $C_{1-6}$ alkyl, $C_{3-10}$ cycloalkyl, aryl, benzyl, heteroaryl, halogen, CN, $CF_3$, $CONR_5R_5$, $S(O)_{0-2}NR_5R_5$, $CSNH_2$;

$X_1$ is selected from alkyl, alkoxy, $R_5$—$C_{3-8}$ membered ring containing C, O, S and/or N, optionally substituted with one or more $R_7$; and $X_2$ is H;

$X_3$ is independently C, $CR_7$, N, $NR_7$;

and pharmaceutically acceptable salts thereof; and (b) detecting a signal from said probe.

2. The method of claim 1, wherein the molecular event is caspase activity.

3. The method of claim 1, wherein the detecting step is with positron emission tomography (PET).

4. The method of claim 1, wherein the compound is of the following formula:

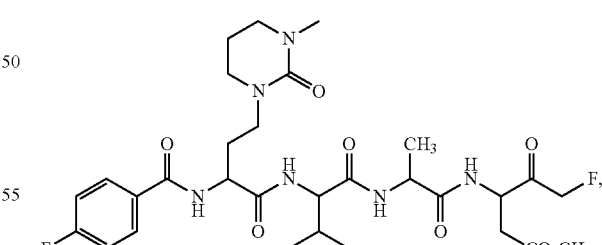

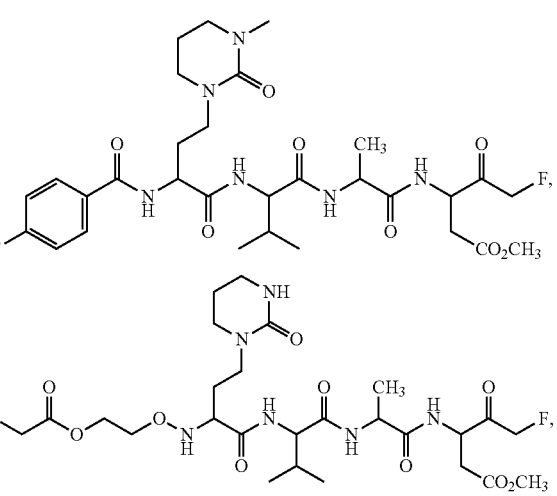

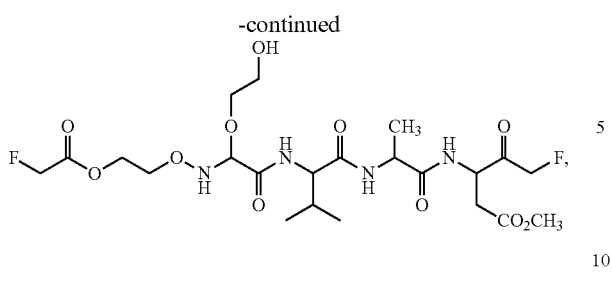

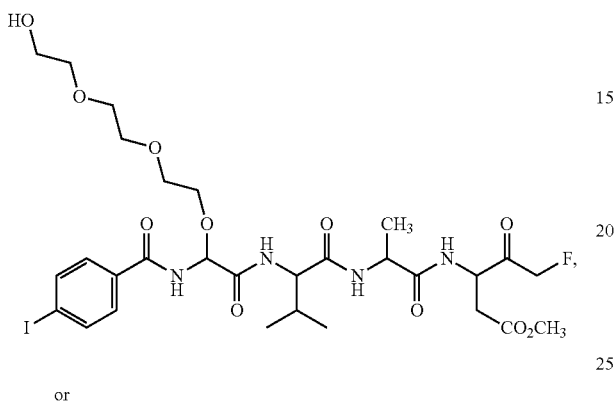

or

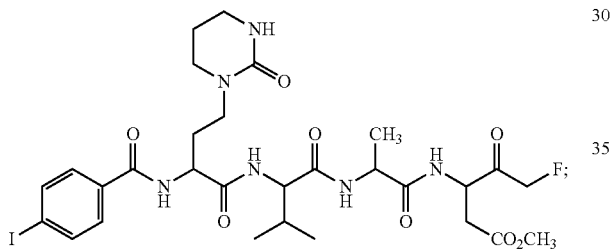

or a pharmaceutically acceptable salt thereof.

5. The method of claim 1, wherein said sample is at least one of cells, tissue, cellular tissue, serum, cell extract, bodily fluids and wherein the administration step is in vivo or in vitro.

6. The method of claim 1, wherein said molecular event is at least one of cell proliferation, apoptosis, and caspase activity.

7. A compound of the following formula:

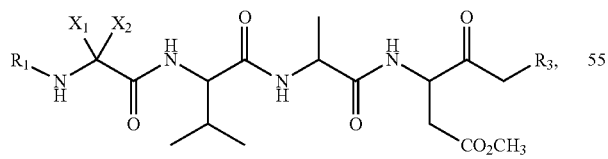

wherein:

$R_1$ is selected from (i) alkyl-halogen, CO-alkyl-halogen, CO-phenyl, CO-alkyl-phenyl, CO-pyridinyl, wherein alkyl is optionally substituted with one or more $R_7$, and phenyl or pyridinyl is optionally halogen-substituted;

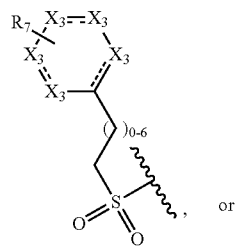

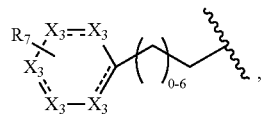

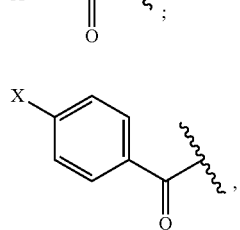

(ii)

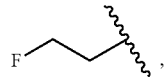

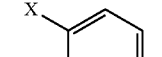

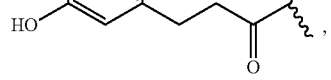

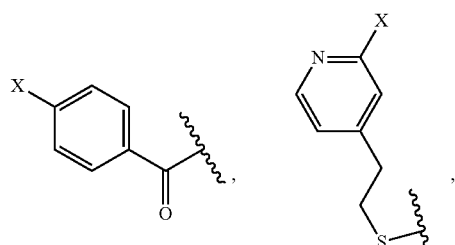

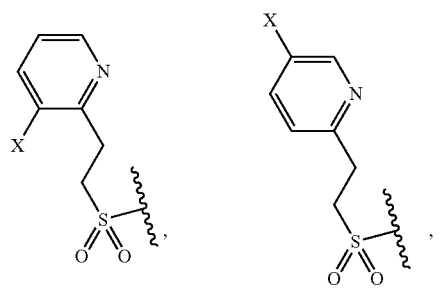

-continued

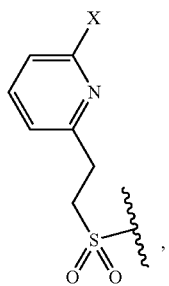

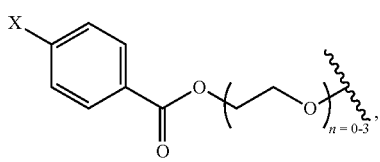

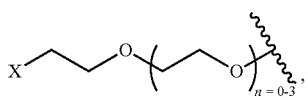

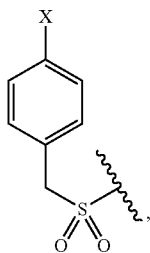

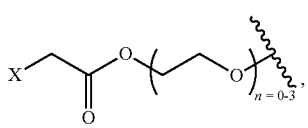

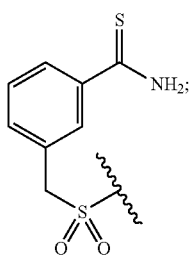

X is iodine or fluorine;

$R_3$ is halogen;

$R_5$ is selected from alkyl, alkoxy;

$R_7$ is selected from hydrogen, $C_{1-6}$ alkyl, $C_{3-10}$ cycloalkyl, aryl, benzyl, heteroaryl, halogen, CN, $CF_3$, $CONR_5R_5$, $S(O)_{0-2}NR_5R_5$, $CSNH_2$;

$X_1$ is selected from alkyl, alkoxy, $R_5$—$C_{3-8}$ membered ring containing C, O, S and/or N, optionally substituted with one or more $R_7$; and $X_2$ is H;

$X_3$ is independently C, $CR_7$, N, $NR_7$;

and pharmaceutically acceptable salts thereof.

8. The compound of claim 7, of the following formula:

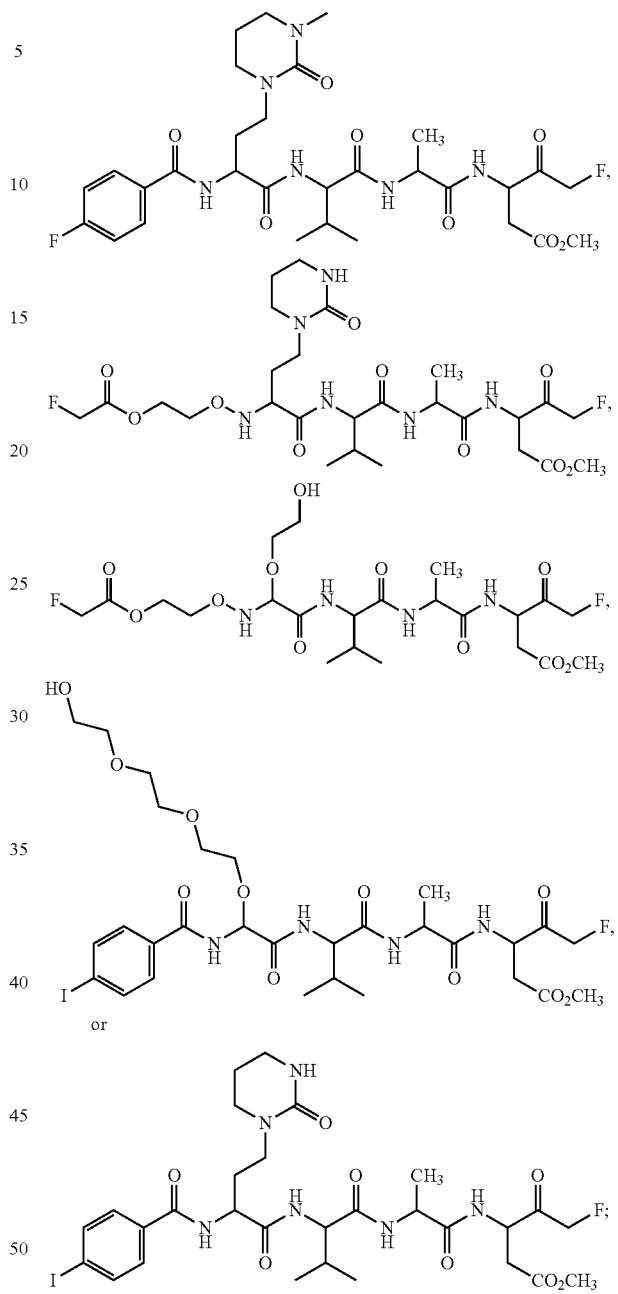

and pharmaceutically acceptable salts thereof.

9. A method of quantifying the progression of a disease state in a subject, comprising:
(a) administering to a first sample of the subject a probe having an affinity for a target, the probe comprising a compound of the following:

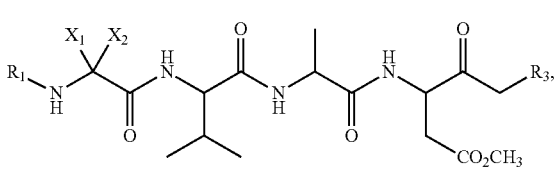

wherein:

R₁ is selected from
(i) alkyl-halogen, CO-alkyl-halogen, CO-phenyl, CO-alkyl-phenyl, CO-pyridinyl, wherein alkyl is optionally substituted with one or more R₇, and phenyl or pyridinyl is optionally halogen-substituted;

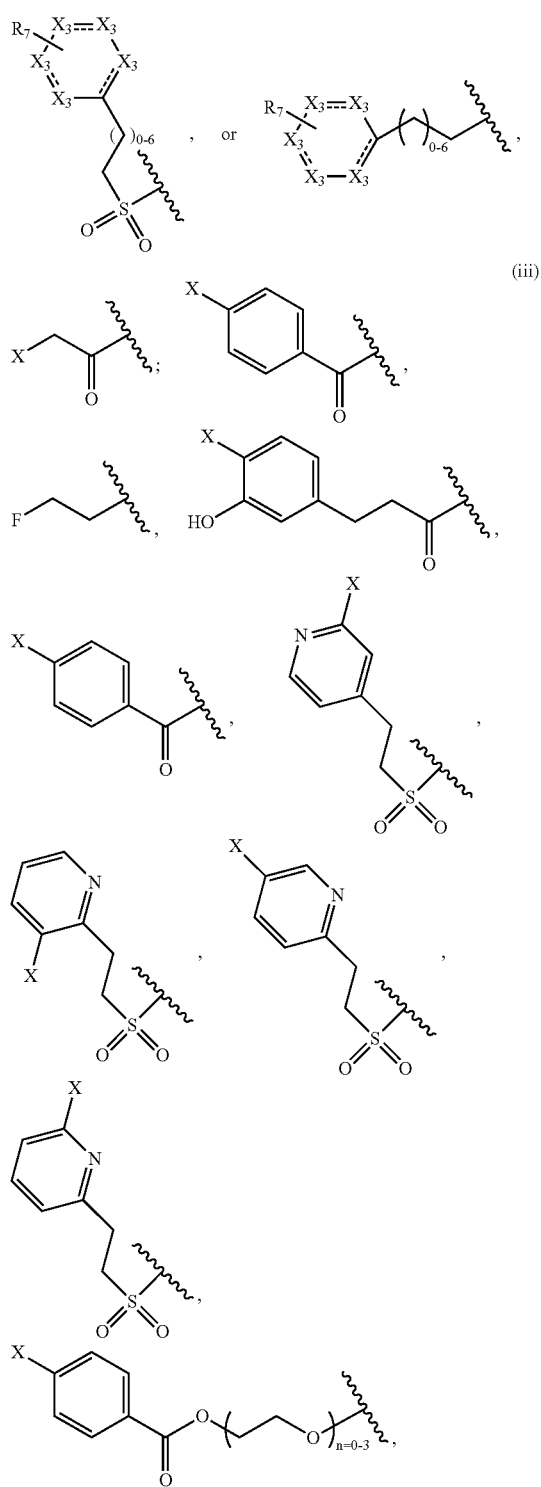

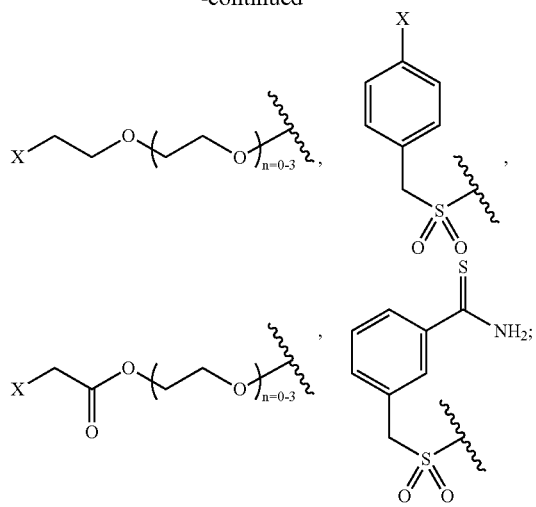

X is iodine or fluorine;
R₃ is halogen;
R₅ is selected from alkyl, alkoxy;
R₇ is selected from hydrogen, $C_{1-6}$ alkyl, $C_{3-10}$ cycloalkyl, aryl, benzyl, heteroaryl, halogen, CN, CF₃, CONR₅R₅, $S(O)_{0-2}NR_5R_5$, CSNH₂;
X₁ is selected from alkyl, alkoxy, R₅-$C_{3-8}$ membered ring containing C, O, S and/or N, optionally substituted with one or more R₇; and
X₂ is H;
X₃ is independently C, CR₇, N, NR₇;
and pharmaceutically acceptable salts thereof;
(b) detecting a signal from said probe;
(c) after a period of time from step (b), administering to a second sample of the subject a probe having an affinity for a target, the probe comprising a compound of the following:

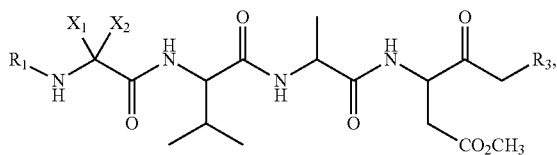

wherein:
R₁ is selected from
(i) alkyl-halogen, CO-alkyl-halogen, CO-phenyl, CO-alkyl-phenyl, CO-pyridinyl, wherein alkyl is optionally substituted with one or more R₇, and phenyl or pyridinyl is optionally halogen-substituted;

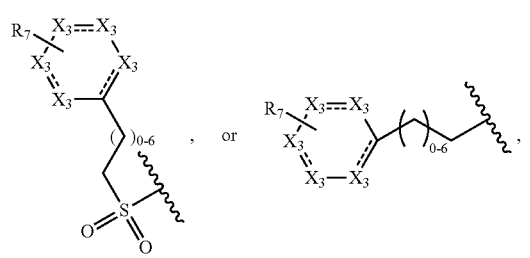

-continued (iii)

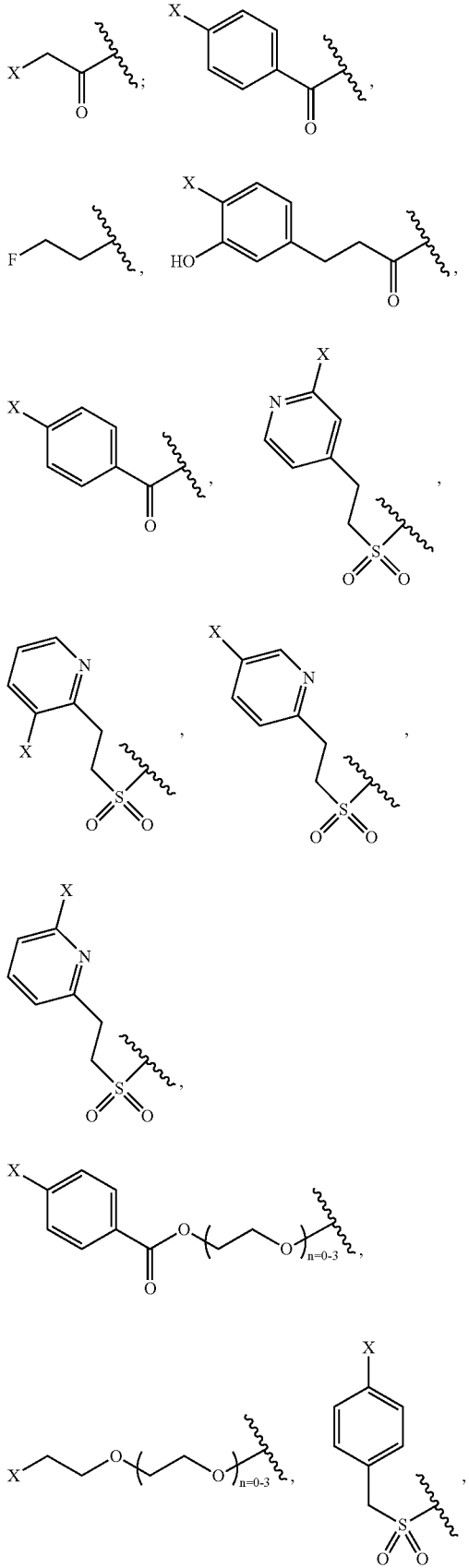

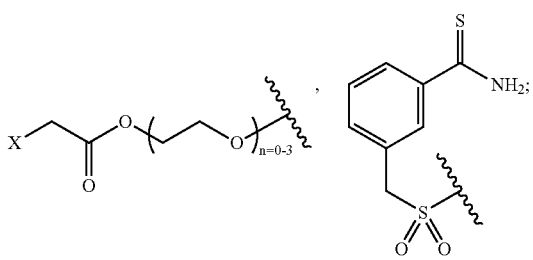

X is iodine or fluorine;

R₃ is halogen;

R₅ is selected from alkyl, alkoxy;

R₇ is selected from hydrogen, $C_{1-6}$ alkyl, $C_{3-10}$ cycloalkyl, aryl, benzyl, heteroaryl, halogen, CN, $CF_3$, $CONR_5R_5$, $S(O)_{0-2}NR_5R_5$, $CSNH_2$;

X₁ is selected from alkyl, alkoxy, $R_5$-$C_{3-8}$ membered ring containing C, O, S and/or N, optionally substituted with one or more R₇; and X₂ is H;

X₃ is independently C, CR₇, N, NR₇; and pharmaceutically acceptable salts thereof;

(d) detecting a second signal; and (e) comparing the first signal with the second signal to determine the progress of a disease state.

10. The method of claim 9, wherein said sample is at least one of cells, tissue, cellular tissue, serum, cell extract, bodily fluid.

11. The method of claim 9, wherein the probe is a compound of the following formula:

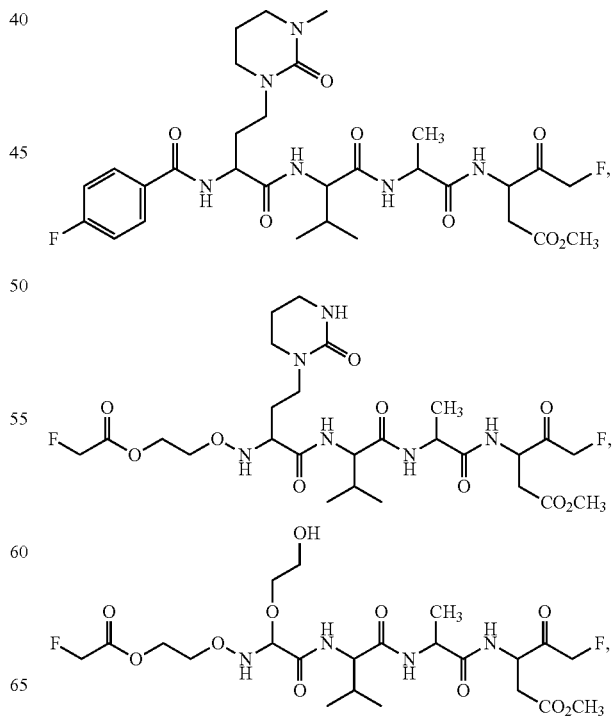

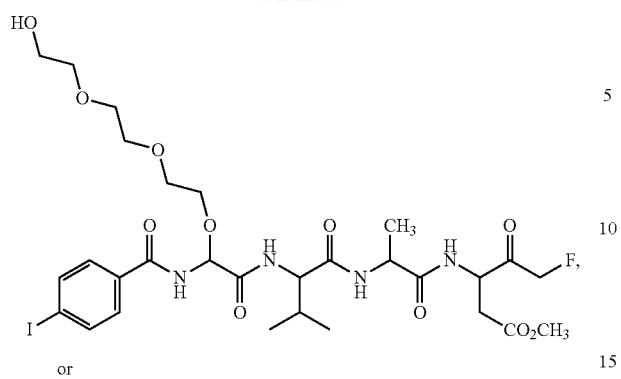

or

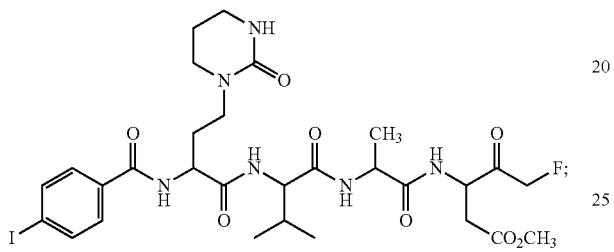

or a pharmaceutically acceptable salt thereof; and a pharmaceutical carrier.

12. A method of determining the presence of a disease state, comprising:
(a) administering to a first sample of the subject a probe having an affinity for a target, the probe comprising a compound of the following:

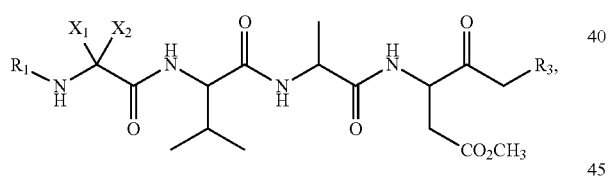

wherein:

$R_1$ is selected from (i) alkyl-halogen, CO-alkyl-halogen, CO-phenyl, CO-alkyl-phenyl, CO-pyridinyl, wherein alkyl is optionally substituted with one or more $R_7$, and phenyl or pyridinyl is optionally halogen-substituted;

(ii)

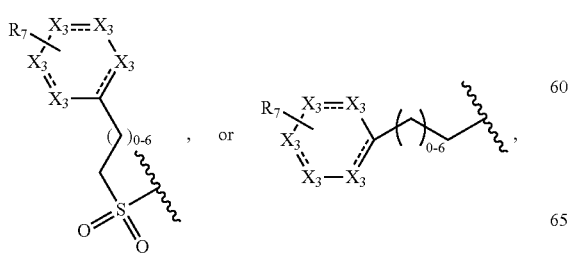

(iii)

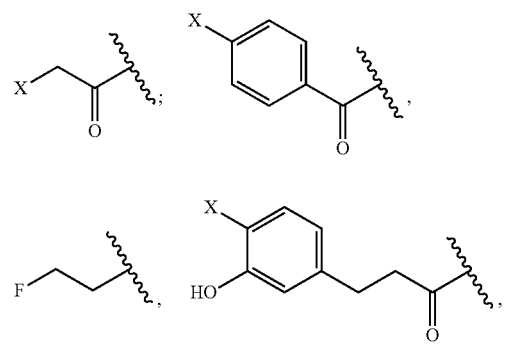

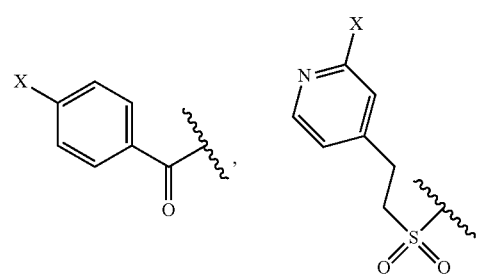

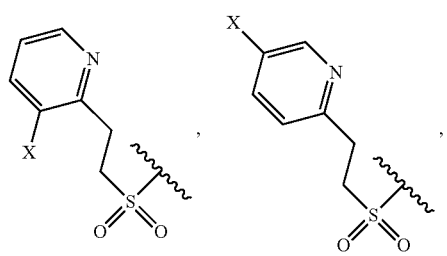

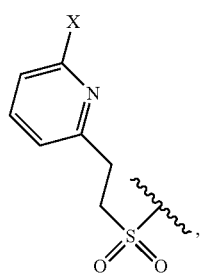

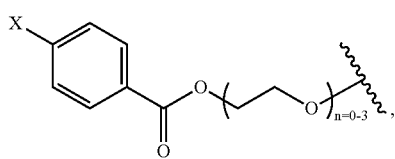

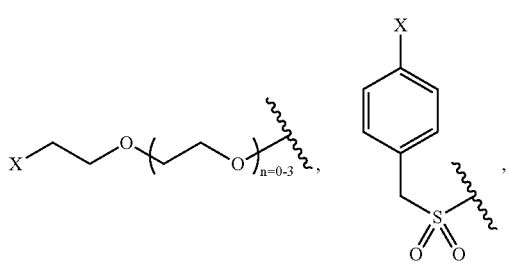

-continued

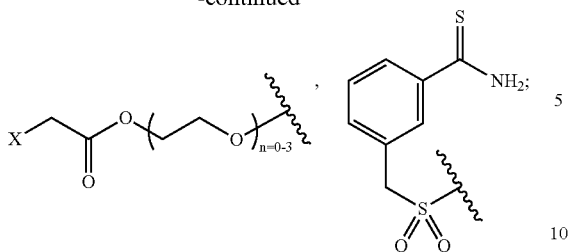

X is iodine or fluorine;
R$_3$ is halogen;
R$_5$ is selected from alkyl, alkoxy;
R$_7$ is selected from hydrogen, C$_{1-6}$ alkyl, C$_{3-10}$ cycloalkyl, aryl, benzyl, heteroaryl, halogen, CN, CF$_3$, CONR$_5$R$_5$, S(O)$_{0-2}$NR$_5$R$_5$, CSNH$_2$;
X$_1$ is selected from alkyl, alkoxy, R$_5$-C$_{3-8}$ membered ring containing C, O, S and/or N, optionally substituted with one or more R$_7$; and
X$_2$ is H;
X$_3$ is independently C, CR$_7$, N, NR$_7$;
and pharmaceutically acceptable salts thereof;
(b) detecting a signal from said probe.

13. The method of claim 12 further comprising a disease state treatment step either before step (a), after step (b), or both.

14. The method of claim 12, wherein the disease state is cancer.

* * * * *

UNITED STATES PATENT AND TRADEMARK OFFICE
CERTIFICATE OF CORRECTION

PATENT NO. : 10,294,271 B1
APPLICATION NO. : 14/183480
DATED : May 21, 2019
INVENTOR(S) : Manning et al.

Page 1 of 1

It is certified that error appears in the above-identified patent and that said Letters Patent is hereby corrected as shown below:

In the Specification

Replace the second paragraph titled government interest, which appears on Column 1, with the following:

Government Support
This invention was made with government support under grant numbers CA140628, CA145138, CA127349, CA128323, CA095103, CA126588, RR017858, MH085768, DK058404 and CA136440 awarded by the National Institutes of Health. The government has certain rights in the invention.

Signed and Sealed this
Seventeenth Day of December, 2019

Andrei Iancu
*Director of the United States Patent and Trademark Office*